United States Patent
Hoke-Kearns et al.

(10) Patent No.: US 10,039,895 B2
(45) Date of Patent: Aug. 7, 2018

(54) THERMAL MATERIAL NEBULIZING SYSTEM

(71) Applicants: Melissa K. Hoke-Kearns, Quilcene, WA (US); Paula G. Sorbel, Port Townsend, WA (US); Justin P. Curran, Anacortes, WA (US)

(72) Inventors: Melissa K. Hoke-Kearns, Quilcene, WA (US); Paula G. Sorbel, Port Townsend, WA (US); Justin P. Curran, Anacortes, WA (US)

(73) Assignee: SATORI INNOVATIONS CORPORATION, Port Townsend, WA (US)

(*) Notice: Subject to any disclaimer, the term of this patent is extended or adjusted under 35 U.S.C. 154(b) by 0 days.

(21) Appl. No.: 14/199,821

(22) Filed: Mar. 6, 2014

(65) Prior Publication Data
US 2014/0251319 A1    Sep. 11, 2014

Related U.S. Application Data

(60) Provisional application No. 61/773,603, filed on Mar. 6, 2013.

(51) Int. Cl.
*A61M 11/02* (2006.01)
*A61M 16/00* (2006.01)
(Continued)

(52) U.S. Cl.
CPC .......... *A61M 16/1085* (2014.02); *A61D 7/04* (2013.01); *A61M 16/0833* (2014.02); *A61M 16/14* (2013.01); *A61M 16/16* (2013.01); *A62B 9/003* (2013.01); *A61M 11/06* (2013.01); *A61M 16/06* (2013.01); *A61M 16/0875* (2013.01); *A61M 2205/3606* (2013.01); *A61M 2250/00* (2013.01)

(58) Field of Classification Search
CPC .......... A61M 16/1085; A61M 16/0833; A61M 16/16; A61M 16/14; A61M 11/06; A61M 2250/00; A61M 2205/3606; A61M 16/06; A61M 16/0875; A61D 7/04; F25D 3/08; F25D 31/006; F25D 2331/8014; B65D 51/24; A61J 9/04; A61J 9/00
USPC .......... 128/200.14, 200.18, 203.12, 204.15, 128/206.23; 119/65, 420, 831; 220/592.01, 592.16, 212, 705, 703, 709; 62/457.1, 457.2
See application file for complete search history.

(56) References Cited

U.S. PATENT DOCUMENTS 2,035,213 A * 3/1936 Anderson ............... F28D 7/026
165/104.19
2,960,985 A * 11/1960 Wiese, Jr. ................ 128/203.25
(Continued)

FOREIGN PATENT DOCUMENTS

FR    2 481 122 A1    10/1981

*Primary Examiner* — Justine Yu
*Assistant Examiner* — Douglas Sul
(74) *Attorney, Agent, or Firm* — Seed IP Law Group LLP

(57) ABSTRACT

A system for thermal regulation of a nebulizer is provided. The system includes a container to house a nebulizer and a thermal material together. The thermal material acts to chill a liquid located inside the nebulizer, in order to deliver a chilled mist to a patient for therapeutic purposes, such as initiating. Therapeutic Hypothermia, or treating various respiratory illnesses such as croup, laryngobronchitis, and smoke inhalation.

14 Claims, 20 Drawing Sheets

(51) Int. Cl.
*A61M 16/10* (2006.01)
*A61D 7/04* (2006.01)
*A61M 16/14* (2006.01)
*A62B 9/00* (2006.01)
*A61M 16/16* (2006.01)
*A61M 16/06* (2006.01)
*A61M 16/08* (2006.01)
*A61M 11/06* (2006.01)

(56) References Cited

U.S. PATENT DOCUMENTS

| | | | |
|---|---|---|---|
| 3,140,590 A | 7/1964 | Gleockler | |
| 3,733,060 A | 5/1973 | Merritt | |
| 3,990,441 A | 11/1976 | Hoyt et al. | |
| 4,519,219 A * | 5/1985 | Prepodnik | F25D 3/06 |
| | | | 206/519 |
| 4,593,688 A | 6/1986 | Payton | |
| 4,595,002 A | 6/1986 | Michaels et al. | |
| 4,882,914 A * | 11/1989 | Haines-Keeley et al. | 62/457.4 |
| 5,146,757 A | 9/1992 | Dearing | |
| 5,177,981 A * | 1/1993 | Haas | A47G 19/2288 |
| | | | 62/1 |
| 5,406,808 A * | 4/1995 | Babb | A47J 41/0005 |
| | | | 220/379 |
| 5,542,413 A | 8/1996 | Horn | |
| 5,555,746 A * | 9/1996 | Thompson | B65D 25/2811 |
| | | | 215/396 |
| 5,605,146 A | 2/1997 | Särelä | |
| 5,630,409 A | 5/1997 | Bono et al. | |
| 5,655,520 A | 8/1997 | Howe et al. | |
| 5,673,690 A * | 10/1997 | Tayebi et al. | 128/206.24 |
| 5,685,291 A * | 11/1997 | Marsh | 128/200.15 |
| 5,906,198 A | 5/1999 | Flickinger | |
| 6,138,672 A | 10/2000 | Kankkunen | |
| 6,244,576 B1 | 6/2001 | Tsai | |
| 6,349,725 B1 | 2/2002 | Perkins et al. | |
| 6,467,299 B1 * | 10/2002 | Coetzee | A61J 1/165 |
| | | | 62/371 |
| 6,530,374 B1 | 3/2003 | Ferraro | |
| 6,536,423 B2 | 3/2003 | Conway | |
| 6,568,202 B1 | 5/2003 | Hodges | |
| 6,571,574 B1 | 6/2003 | Blackstone | |
| 6,585,123 B1 * | 7/2003 | Pedmo | B65D 1/0276 |
| | | | 206/509 |
| 6,588,621 B2 * | 7/2003 | Shimazaki | F25D 3/08 |
| | | | 220/23.89 |
| 6,901,769 B2 | 6/2005 | Blackstone | |
| 6,997,184 B2 * | 2/2006 | Donohue | 128/204.15 |
| 7,117,690 B1 * | 10/2006 | Dunn et al. | 62/457.1 |
| 7,201,163 B2 | 4/2007 | Jiang et al. | |
| 7,267,120 B2 | 9/2007 | Rustad et al. | |
| 7,559,491 B1 * | 7/2009 | Chang | B05B 7/2424 |
| | | | 128/200.18 |
| 8,573,198 B2 * | 11/2013 | Riggs et al. | 128/202.17 |
| 2006/0191284 A1 * | 8/2006 | Fuller | F25D 31/006 |
| | | | 62/389 |
| 2007/0163575 A1 | 7/2007 | Rojas, Jr. | |
| 2008/0229609 A1 | 9/2008 | Bronshtein | |
| 2008/0262377 A1 | 10/2008 | Belson | |
| 2009/0020124 A1 | 1/2009 | Roth et al. | |
| 2009/0056716 A1 | 3/2009 | Carrier | |
| 2009/0071470 A1 | 3/2009 | Abrams | |
| 2009/0107491 A1 | 4/2009 | Belson | |
| 2009/0165786 A1 | 7/2009 | Barbut et al. | |
| 2010/0031957 A1 | 2/2010 | McIntosh et al. | |
| 2011/0005522 A1 | 1/2011 | Vervoort | |
| 2011/0009809 A1 | 1/2011 | Bielfeldt et al. | |
| 2012/0125335 A1 * | 5/2012 | Affinito | 128/204.15 |

* cited by examiner

THERMAL MATERIAL NEBULIZING SYSTEM

BACKGROUND

Technical Field

The present disclosure relates to devices for atomizing liquid and, more particularly, to a noninvasive portable apparatus and system that utilizes a thermal medium to chill atomized liquid into a stream of chilled mist during nebulization.

Description of the Related Art

Nebulizers are commonly found in the healthcare industry for delivery of atomized mist to a patient. Nebulizers hold a prescribed amount of liquid medication or saline that is then atomized for inhalation. The medication used will vary, depending on the needs of the patient, which can range from Albuterol for Asthma to Racemic Epinephrine for Croup. Nebulizers utilize a variety of technologies to atomize the solutions being inhaled, such as jet nebulizers, High Density Jet Nebulizers, ultrasonic wave nebulizers, and ultrasonic vibrating mesh technology among others. These methods all produce a room temperature mist delivered to the patient's airway, usually particles fewer than 5 micrometers for better delivery to the patient's airway.

Nebulizers are used for a variety of conditions including but not limited to Croup, RSV, Epiglottitis, Allergic Reactions, Bronchospasm, Laryngitis, Pneumonia, Asthma, COPD, Bronchitis, Sepsis, ventilated patients, and smoke/heat/blast inhalation patients. They are commonly used by Emergency Medical Services (EMS) Pre-Hospital, ambulance, medical flight crews in aircraft, in Emergency Departments, ICU's, CCU's, Operating rooms, Recovery rooms, Medical and Surgical units, Respiratory Therapy for both in and out patients, Medical Short Stay units, doctors' offices, urgent care clinics, Home Health, Military Medical personal in military hospitals, field hospitals, and front line medic treatment, Wilderness expedition medical crews, World Outreach Medical Teams, individual patients in their homes and by Veterinarians in Animal Hospitals, Zoos, Clinics, and in Outpatient settings.

Chilled liquid nebulized into mist can have beneficial effects on the patient and can be more comfortable for the patient. Chilled liquid nebulized into mist can act to reduce swelling and irritation of the larynx and upper respiratory tract due to illness such as croup, bronchitis, allergic reaction, smoke inhalation and other airway compromised patients. Chilled liquid nebulized into mist can act to initiate Therapeutic Hypothermia and treat other heat related illness.

Attempts have been made to chill breathable gases in the past, for example those of U.S. Pat. No. 6,536,423 ("Conway"), U.S. Pat. No. 6,997,184 ("Donohue"), U.S. Pat. No. 7,201,163 ("Jiang et al") and U.S. patent application Ser. No. 11/899,110 ("Carrier"). However, these attempts have all failed to produce an adaptable, ergonomic, highly portable, simple way to produce chilled mist nebulized from chilled liquid. For example, Conway uses a complicated mist producing apparatus that requires a constant power supply and is not compatible with standard nebulizers. Donohue cannot interface with a nebulizer and, therefore, cannot chill the fine mist produced by a nebulizer. Furthermore, Donohue chills the air that is breathed in immediately prior to breathing in, which may cause significant condensation of any fine particles contained in the air, significantly reducing the benefits of breathing fine particles. Similarly, Jiang et al uses a complex heat exchanger in order to chill or heat the mist and is not compatible with standard nebulizers in a portable manner. Carrier also does not interface with a standard nebulizer, and his device produces the chilling effect immediately prior to inhalation, which can cause the condensation issues described above. Carrier also involves a number of separate pieces that must be placed together in order to use the device, greatly reducing simplicity and ease of use.

Moreover, these designs require complicated processes and setups, and none are readily compatible with standard small-volume nebulizers, therefore requiring additional costly devices. There is a need, therefore, for a simple, ergonomic solution to chill the nebulized mist coming from a standard nebulizer, without requiring expensive or complicated systems. Such a solution should address the need for rapid reduction of airway edema, irritation, and/or inflammation in patients with Epiglottis, Croup, RSV, Bronchospasm, Fever, Allergic Reaction, Smoke Inhalation, Blast Injury, Asthma, Bronchitis, Pneumonia, Laryngitis, Sepsis, COPD, ventilated patients, and pre and post ENT surgery, as well as provide for core cooling during CPR. Moreover, there is a need for rapid initiation of Therapeutic Hypothermia for patients post Cardiac Arrest or acute brain insult. Furthermore, there is a need for Targeted Temperature Management (TTM).

BRIEF SUMMARY

In accordance with one embodiment of the present disclosure, a thermal nebulizing system is disclosed. The thermal nebulizing system includes a device that has a container with an interior, an input port in fluid communication with the interior, a nebulizer in the interior of the container and coupled to the input port, a conduit coupled to the nebulizer and configured to deliver a mist from the nebulizer to the exterior of the container, and a lid configured to cover the container. The interior is configured to accept a thermal material for cooling.

In another embodiment, the device has a thermal material configured to chill a liquid; a source configured to deliver at least one of oxygen or compressed air to the nebulizer; and a delivery mechanism configured to interface with a recipient and deliver chilled nebulized mist from the nebulizer to the recipient. In a further embodiment, the thermal material is an evaporative material.

In accordance with one aspect of the present disclosure, a device is provided that includes a container having at least a side wall and a bottom wall configured to define an open interior and an open top in communication with the interior, and an input port in the bottom wall or the side wall that is in fluid communication with the interior; a nebulizer located in the interior of the container and coupled to the input port for fluid communication; a lid configured to cover the open top and provide fluid communication with the interior of the container; and a conduit coupled to the lid and the nebulizer and configured to deliver a chilled mist from the nebulizer through the access tube extending through the lid to an exterior of the container.

In accordance with another aspect of the present disclosure, the device includes a nipple extending through the container input port and into the interior of the container, the nipple coupled to an input of the nebulizer and sized and shaped to provide fluid communication between the input port and the input of the nebulizer and to position the nebulizer above the bottom wall of the container.

In accordance with a further aspect of the present disclosure, the device includes a delivery apparatus coupled to the conduit that includes a mask having a body with an interior chamber and a cap with radially oriented flaps that are capable of bending inward into the interior chamber, the interior chamber sized and shaped to accommodate the muzzle, snout or beak of an animal.

In accordance with still yet another aspect of the present disclosure, a system is provided that includes a thermal material configured to chill a liquid; a nebulizing device; a hand-holdable container having an interior sized and shaped to receive the nebulizing device and configured to store the thermal material around the nebulizing device; a source configured to deliver at least one of oxygen or compressed air to an input of the nebulizing device; and a delivery apparatus operably coupled to an output of the nebulizing device and configured to interface with a recipient and deliver chilled nebulized mist from the nebulizing device to the recipient.

Ideally, the system includes a conduit extending through the container and into the interior of the container, the conduit coupled to the input of the nebulizing device and sized and shaped to provide fluid communication between the source and the input of the nebulizing device and to hold the nebulizing device above the bottom wall of the container.

In accordance with still yet a further aspect of the present disclosure, a thermal material nebulizing and delivery apparatus is provided that includes a nebulizer having a fluid input and a fluid output and configured to hold a liquid; thermal material; a container configured to hold the thermal material and the nebulizer, the container having an interior and an input port and an open top in fluid communication with the interior and the input port; a cover configured to close the open top and having an opening structured to provide fluid communication with the interior; and a conduit mounted in the opening of the cover and coupled to the nebulizer and configured to deliver a chilled mist from the nebulizer through the lid and to an exterior of the container.

Ideally, the apparatus includes a conduit extending through the container and into the interior of the container, the conduit coupled to the input of the nebulizing device and sized and shaped to provide fluid communication between the source and the input of the nebulizing device and to hold the nebulizing device above the bottom wall of the container.

In accordance with a further aspect of the present disclosure, the container is configured to hold the nebulizer in the interior and the container is configured to hold the thermal evaporative material in the interior surrounding the contained nebulizer. Alternatively, the container includes a double-walled portion having an interior space configured to hold the thermal material.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures or components or both associated with the nebulizing system, including but not limited to the oxygen or air compressor have not been shown or described in order to avoid unnecessarily obscuring descriptions of the embodiments.

Unless the context requires otherwise, throughout the specification and claims that follow, the word "comprise" and variations thereof, such as "comprises" and "comprising" are to be construed in an open inclusive sense, that is, as "including, but not limited to." The foregoing applies equally to the words "including" and "having."

Reference throughout this description to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

Figure 1:
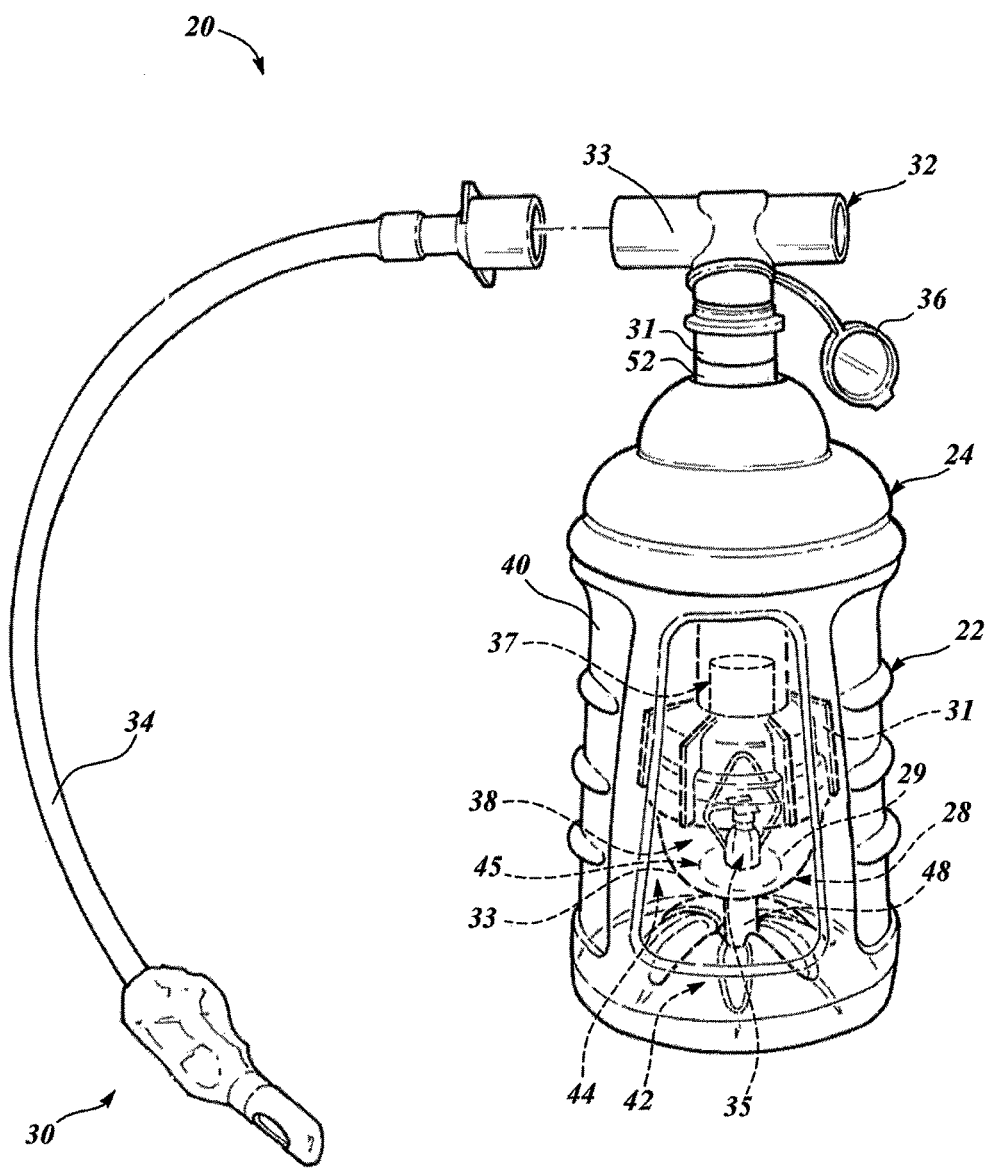
FIG. 1 is an isometric view of a thermal nebulizing device that includes a delivery mechanism according to one embodiment of the present disclosure.

FIG. 1 shows a thermal nebulizing apparatus 20 configured to produce a chilled atomized mist to a patient for therapeutic purposes. The thermal nebulizing system 20 includes a container 22, a lid 24 removably attached to the container, thermal material 26 (shown in FIG. 7) in an interior 44 of the container 22 along with a nebulizer 28, and a delivery mechanism 30. The apparatus 20 also includes a T-shaped connector 32 mounted on top of an access tube 52, and a mist delivery tube 34 configured to be coupled to the connector 32. The thermal nebulizing system 20 provides a number of benefits to patients through the use of the container 22 and thermal material 26. The thermal material 26 acts to cool a liquid 38 that is located in the nebulizer 28, thereby delivering a chilled mist to the patient after nebulization.

Figure 2:
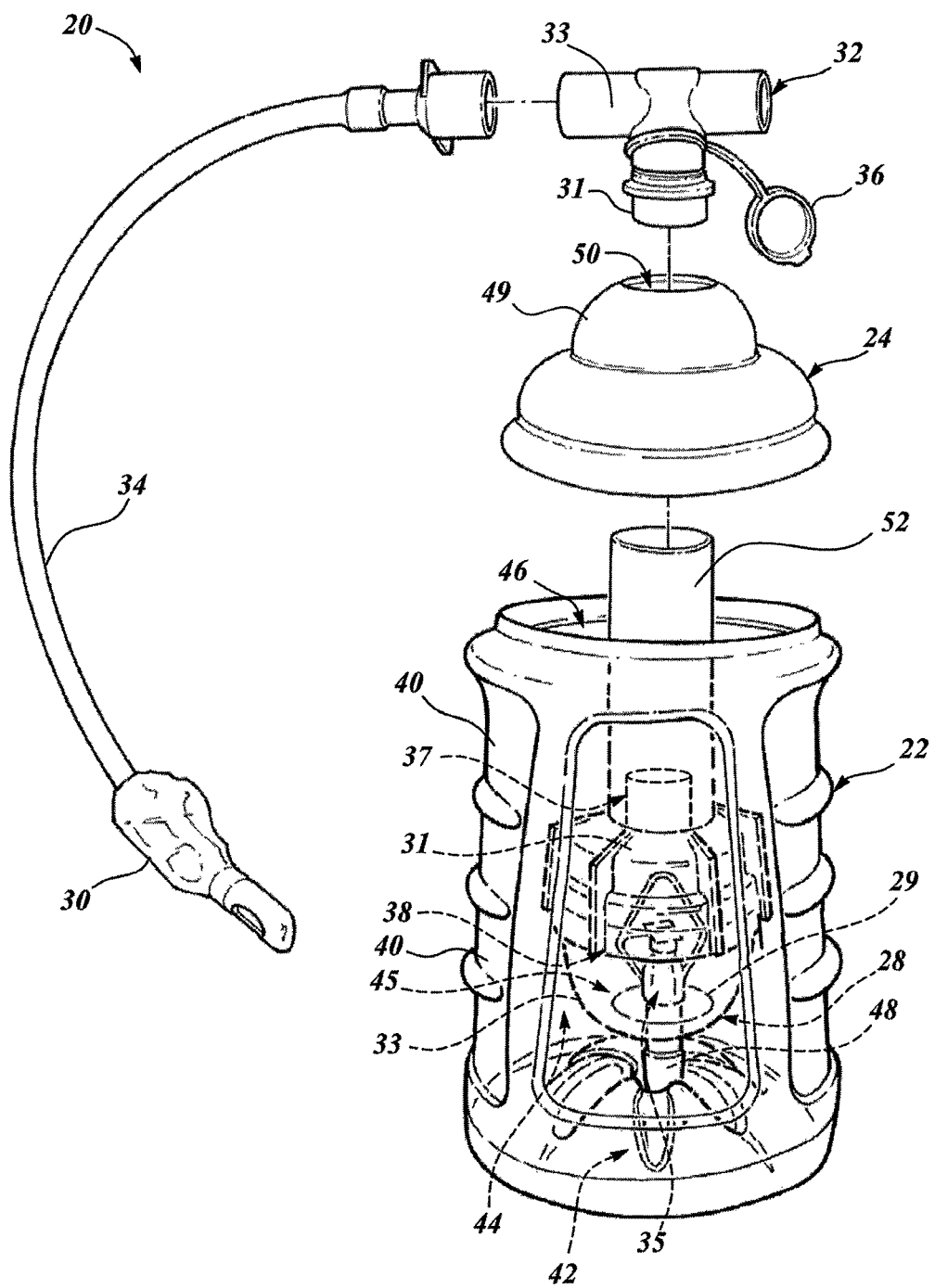
FIG. 2 is a partially exploded isometric view of the device of FIG. 1.
Figure 3:
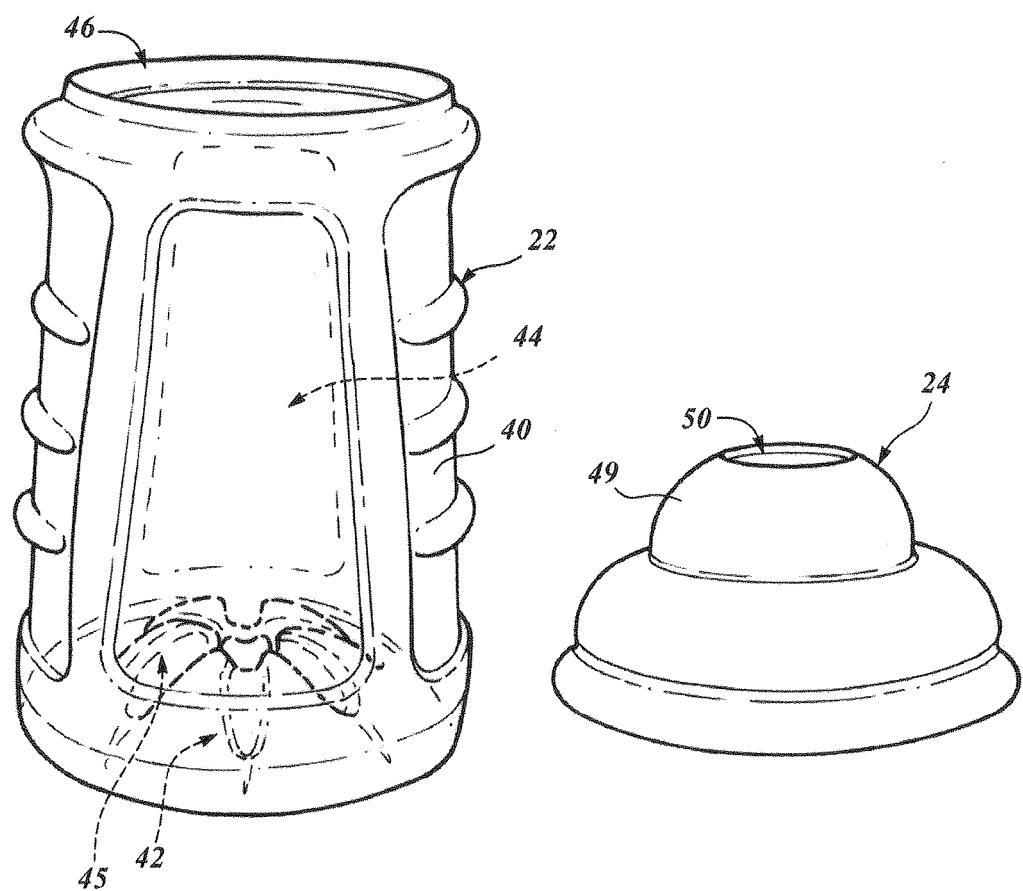
FIG. 3 is an isometric view of a container and cap of the device of FIG. 1.

Referring to FIGS. 1 through 3, the container 22 is made up of a circular sidewall 40 and a bottom 42, forming a substantially hollow interior 44, which is accessible through an opening 46 in the container top. The interior 44 is configured to receive and house the nebulizer 28.

In addition, the interior 44 is structured to receive and store the thermal material 26. The bottom 42 of the container 22 has a connector nipple 48 extending from the interior 44 through to the exterior of the bottom 42, which is structured to provide fluid communication between an interior 45 of the nebulizer 28 and the outside of the container 22. In other embodiments the connector nipple 48 may be located so as to extend through the sidewall 40 of the container 22, or any other suitable location to provide fluid communication between the nebulizer interior 45 and the exterior of the container 22. In some embodiments, the connector nipple 48 may be inserted through and sealingly connected to the container 22 through a snug fitting; however, the nipple 48 may be also be sealingly connected using an adhesive, threading or any other suitable means that provides a seal between the nipple 48 and the container 22 in order to prevent air or liquid from leaking to the outside of the container 22. The ideal embodiment would be injection molded with the nebulizer 28 a fluid part of the container 22 housed in the interior 44 accessed through the opening 46 at the top of the container 22. The access tube 52 is formed to be in fluid communication with the nebulizer 28.

The lid 24 is mounted on to the container 22 in order to close off the opening 46. The lid 24 may be any shape or size, but preferably has a two-tiered convex dome configuration 49. The lid 24 is structured to mount to the sidewall 40 of the container to remain firmly in place yet be removable. The lid 24 may attach to the sidewall 40 through a screw-type threading, or it may snap onto the container 22 using ribs or depressions on the lid 24 and sidewall 40 or by any other suitable means.

The lid 24 includes a tube opening 50 in the top of the dome to accommodate an extension tube or access tube 52, which is configured to provide fluid communication between the nebulizer 28 and the connector 32. The tube opening 50 in the lid 24 has a generally circular shape through which the access tube 52 can be inserted. However, in other embodiments, the tube opening 50 can be any shape and size suitable to accommodate the access tube 52. The access tube 52 is connected to the output of the nebulizer 28 for fluid communication, and it is configured as the output conduit of the nebulizer 28 through which the atomized mist is conveyed and expelled. The access tube 52 is formed to project through the tube opening 50 and connect to a fitting 31 on the connector 32, preferably in a slidable arrangement. The lid 24 with the tube opening 50 and access tube 52 therefore enable fluid communication between the output of the nebulizer 28 and the connector 32 while still closing off the opening 46 of the container 22 to any other fluid communication.

The thermal material 26 (shown in FIG. 7) can be any material with thermal properties capable of inducing a cooling effect on the liquid 38 in the nebulizer 28. The thermal material 26 may induce a cooling effect on the liquid 38. For example, in some cases, a patient may require Therapeutic Hypothermia, in order to cool the temperature of the patient's body. In such a case, the thermal material 26 would be of a type to cool the liquid 38 in order to deliver a chilled mist to the patient. The thermal material 26 is stored in the interior 44 of the container 22, where it thermally interacts with the liquid 38 in the nebulizer 28 in order to induce a cooling effect.

The nebulizer 28 is generally a small volume nebulizer, structured to be inserted into the interior 44 of the container 22. Because the nebulizer 28 is readily commercially available, it will not be described in detail herein. Briefly, the nebulizer 28 can be any type of nebulizer, for example, an ultrasonic nebulizer, jet nebulizer, High Density Jet Nebulizer or vibrating mesh nebulizer, but is preferably a small volume jet nebulizer, such as those manufactured by CareFusion. Generally, the nebulizer 28 has a housing 29 that defines the interior space 45. Typically, the housing 28 is formed of a top 31 and a bottom 33 with a fluid input 35 formed in the bottom 33, which is in fluid communication with the interior space 45, and a fluid output 37 formed in the top 31, which is also in fluid communication with the nebulizer interior space 45. The interior space 45 of the nebulizer 28 contains the liquid 38, which is reduced to a mist of fine particles, and delivered to the patient through the fluid output 37 of the nebulizer and the access tube 52. In all embodiments, the interior space 45 of the nebulizer 28 is in fluid communication with the connector nipple 48. In such an embodiment, the nebulizer 28 receives a gaseous input from a gas source through the connector nipple 48, for example, compressed air or oxygen.

As seen in FIGS. 1 and 2, the nipple 48 extends into the interior 44 of the container 22 a short distance before coupling to the input on the bottom of the nebulizer 28. This positions the nebulizer 28 above the container bottom 48 to be centrally disposed inside the interior 44 of the container 22, permitting the coolant or thermal material to surround the nebulizer 28 from the bottom 33 to the top 31 thereof. This facilitates more rapid and complete cooling of the liquid 38 in the nebulizer 48 as described more fully below.

The delivery mechanism 30 is an interface through which a patient receives the therapeutic mist from the thermal nebulizing system 20. The delivery mechanism 30 is in fluid communication with the nebulizer 28 through the connector 32, either directly or through the tube 34, where the tube is connected to the connector 32 on one end and the delivery mechanism 30 on the other end. In other embodiments, the delivery mechanism may connect directly to the access tube 52. The delivery mechanism 30 is configured to enable a patient to receive the chilled atomized mist through the delivery mechanism 30. There are a number of delivery mechanisms commercially available, such as masks, mouthpieces, endotracheal tubes and pacifier mist delivery devices, and these will not be described in more detail.

The connector 32 is generally a T-shaped connector, but could also be any other connector with two or more end openings, such as an L-shaped connector, a straight tube connector, or a Y-shaped connector. The connector 32 has generally a hollow cylindrical shape, but it could also be any other shape. The fitting 31 extends at substantially a right angle from a cross tube 33, and both the fitting 31 and the cross tube 33 are substantially hollow to allow for air passage. The fitting 31 is structured to connect the access tube 52 to the cross tube 33 and ultimately to the delivery mechanism 30 via the flexible tube 34. The connector 32 may also optionally include a cover 36 in order to close off one of the cross tube 33 openings.

Figure 7:
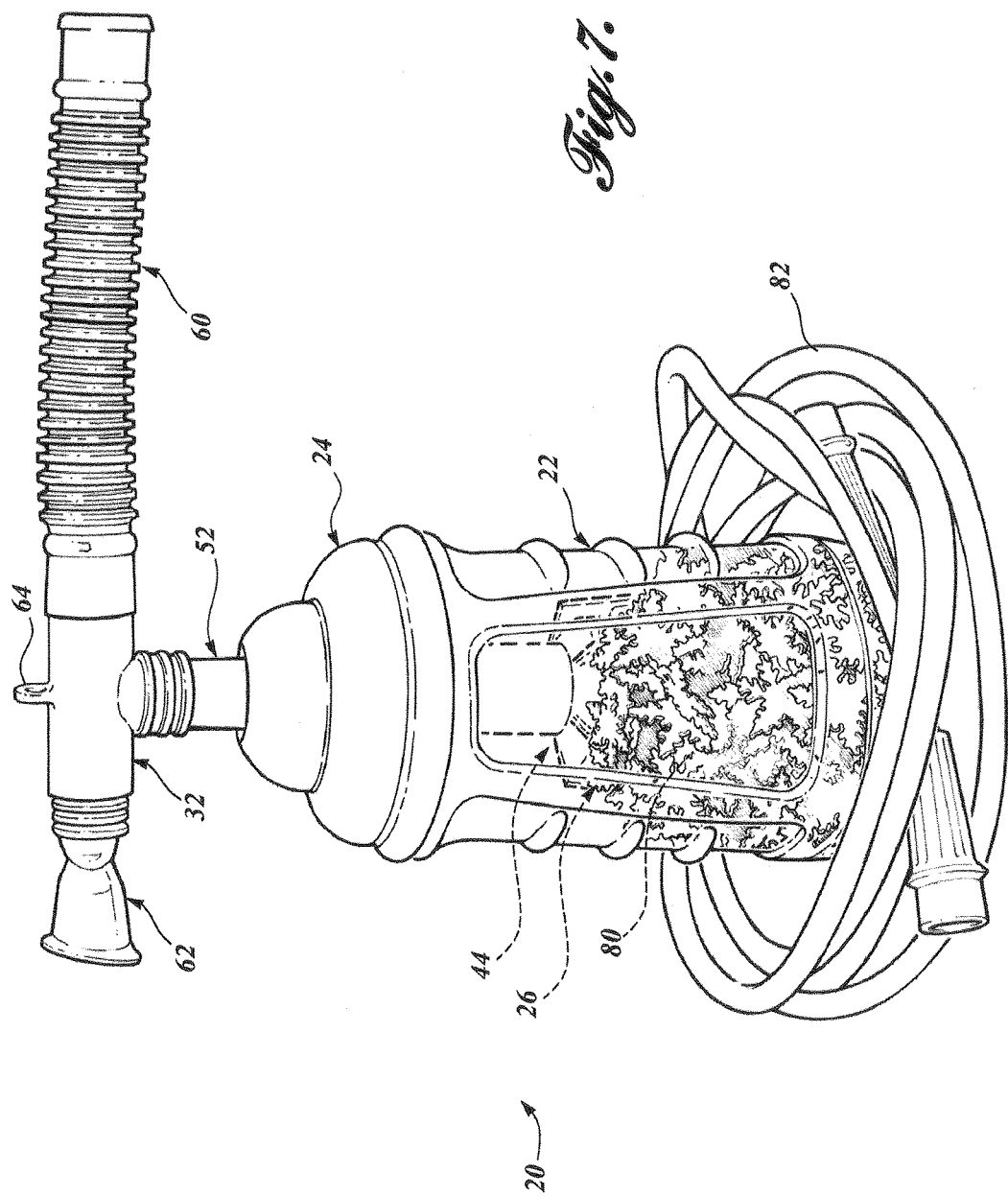
FIG. 7 is an isometric view of a thermal nebulizing device utilizing a thermal evaporative material according to one embodiment of the present disclosure.

In the partially exploded view of FIG. 2, the thermal nebulizing system 20 is assembled by placing the nebulizer 28 inside the container 22, placing the thermal material 26 inside the container 22 (as shown in FIG. 7), and placing the lid 24 on the container 22 to cover the opening 46 while positioning the access tube 52 through the tube opening 50. The connector 32 is attached to the access tube 52, and the delivery mechanism 30 is attached to a connector, to attach to a ventilator. The container 22 may optionally also be covered in a thermally insulating sleeve in order to decrease loss of cooling ability, such as a neoprene sleeve. The nebulizer 28 is then used regularly, either with a liquid medication 38 or with sterile saline, while the patient breathes in the chilled mist through the delivery mechanism 30.

FIG. 3 is an exploded view of the container 22 and lid 24. The container 22 can be any suitable material, but is preferably a material with an insulating quality in order to decrease thermal losses. The container 22 is generally made of a rigid material, such as plastic, polyethylene or polycarbonate, in order to protect the nebulizer 28 and thermal material 26. Other embodiments may use a flexible material for enhanced portability and storage ability when not in use. In some embodiments, the container is between 1.5 and 4 inches in width or diameter, and between 3 and 6 inches in height, preferably about 2.5 inches in width or diameter and about 4.5 inches in height. The opening 46 is generally about the same width as the container 22, or it may be somewhat smaller than the width of the container. Ideally, a 20 ounce size bottle is preferred because anything smaller would not hold enough ice along with the nebulizer 28, and anything much larger would be difficult for a child to hold. The container 22 may be transparent, translucent, or opaque.

The lid 24 is configured to entirely cover and removably attach to the container 22 at the opening 46. The lid 24 may be attached to the container 22 in any suitable fashion, such as threading, rib to rib connection, rib to depression connection, or any other method. The tube opening 50 is configured to snugly fit the access tube 52 through the tube opening 50, and it is generally located in the center of the lid 24. The tube opening 50 may be of any size suitable to fit the access tube 52, but is preferably between 0.5 and 1.5 inches.

Figure 4:
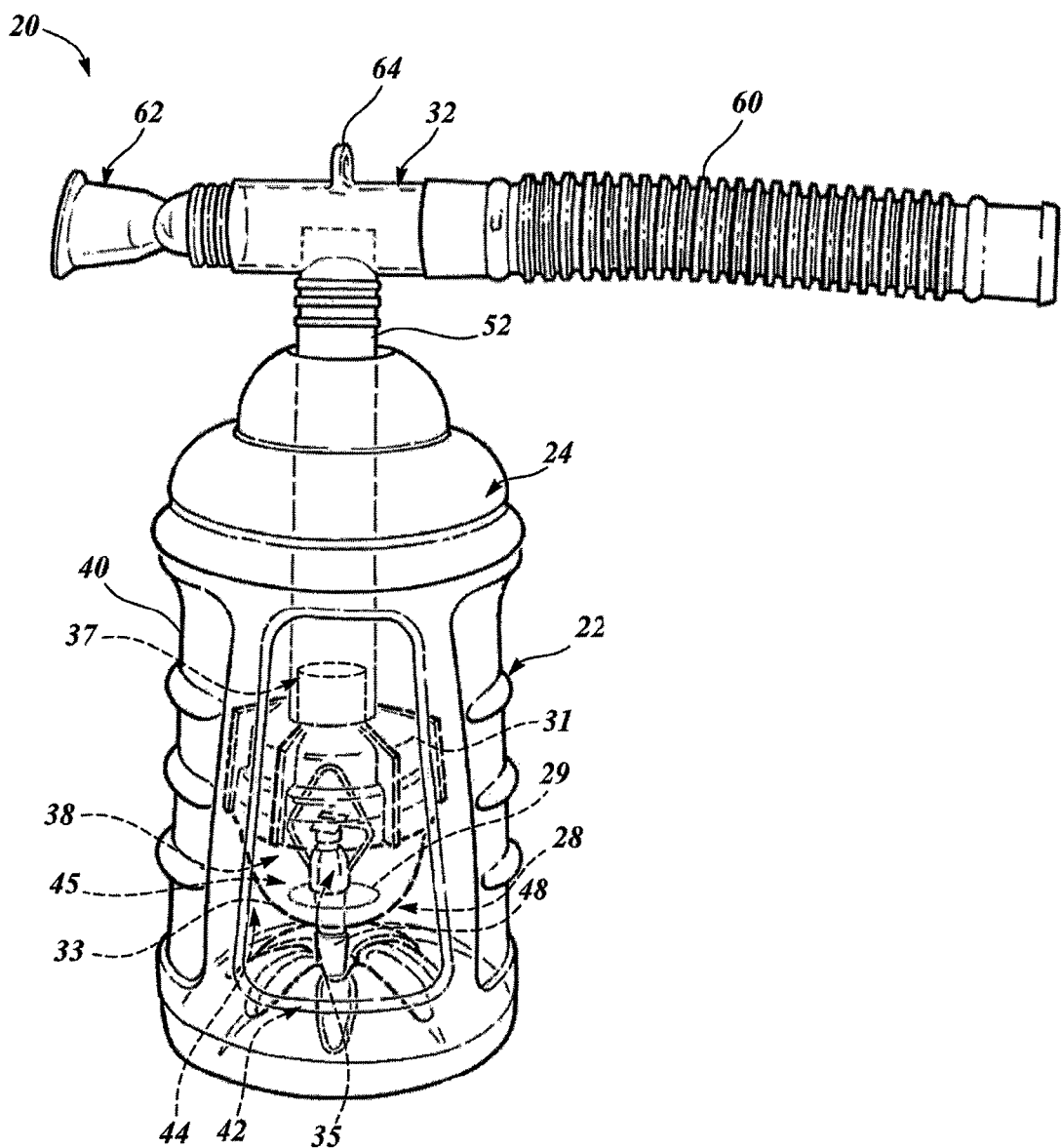
FIG. 4 is an isometric view of a thermal nebulizing device that includes a mouthpiece attached to a connector according to one embodiment of the present disclosure.
Figure 5:
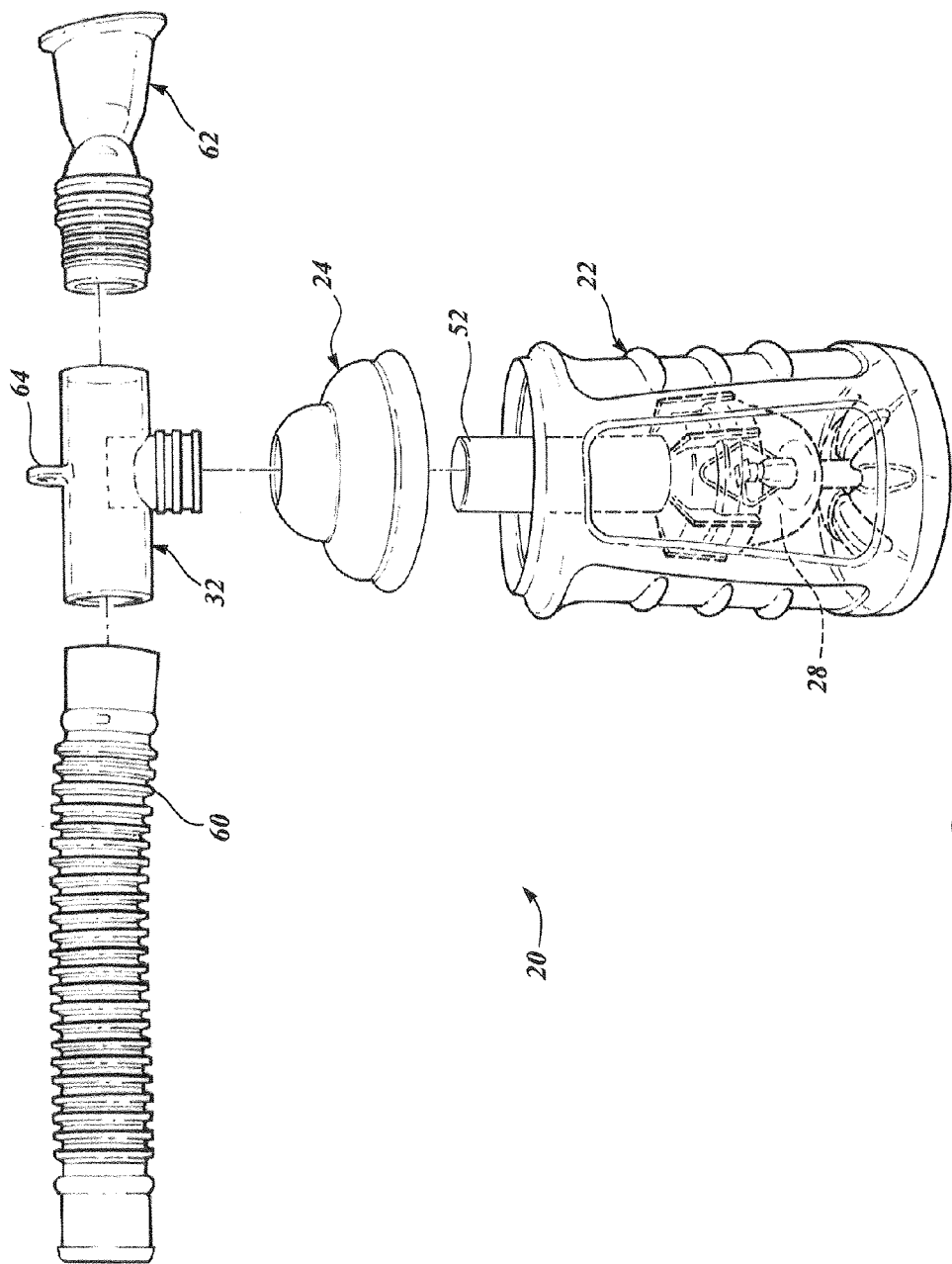
FIG. 5 is a partially exploded isometric view of the nebulizing device of FIG. 4.

FIGS. 4 and 5 show the thermal nebulizing system 20 with a corrugated tube 60 and mouthpiece 62, both of which are readily commercially available. The embodiment shown in FIG. 4 is the preferred embodiment for the typical method of use. The corrugated tube 60 is configured to removably attach to the connector 32, while the mouthpiece 62 attaches to the other end of the connector 32, and is used as the delivery mechanism 30. The corrugated tube 60 allows ambient air to freely mix with the chilled nebulized mist upon delivery when desired. The corrugated tube further allows for the expiration of gases from the thermal nebulizing system 20 when necessary. The mouthpiece 62 is placed into a patient's mouth, and the nebulized mist, or oxygen enriched mist, is then inhaled by the patient through the mouthpiece. The connector 32 may also include an attachment point 64, to which an anchor or tether can be attached to keep the corrugated tube 60 in a desired position.

Figure 6:
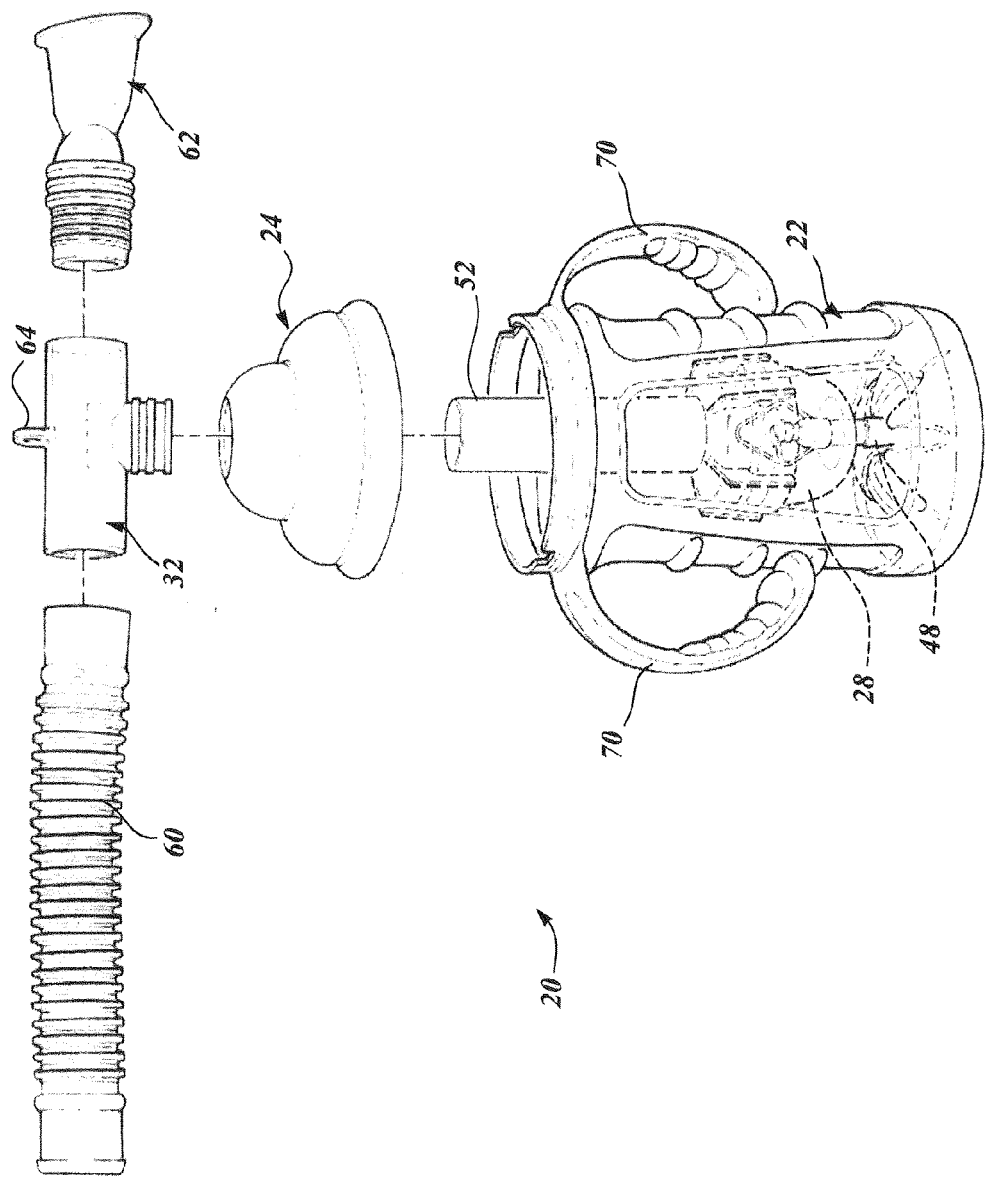
FIG. 6 is a partially exploded isometric view of a thermal nebulizing device with handles according to one embodiment of the present disclosure.

FIG. 6 shows the thermal nebulizing system 20 with at least one handle 70 attached to the container 22. The handle 70 could be place on both sides of the container 22, or the container could have only one handle 70. The handle could be anything suitable to make gripping the container easier, such as a D-shaped piece of rigid material. In some embodiments, the handle 70 is removable, being attached through any suitable removable means, such as a slot/insert mechanism or a hook and loop mechanism, such as Velcro. In other embodiments the handle 70 could be permanently attached to or formed to be integral with the container 22.

FIG. 7 shows the thermal nebulizing system 20 with the thermal material 26, in this case a thermal evaporative material 80 and a tubing 82. The thermal evaporative material 80 is a fast evaporating material that is placed in the interior 44 of the container 22 in order to chill the liquid 38. The evaporative material 80 could be any dry material capable of rapid evaporation to provide a cooling effect, such as evaporative material available from the Shanghai Tianjin Industry Co., Ltd. The thermal evaporative material 80 is activated by adding 30-60 mls water to 12-22 grams of dry snowflake shaped pieces of the evaporative material 80. This allows users to chill the liquid 38 without access to power or ice, making the thermal nebulizing system 20 highly portable and mobile. The thermal evaporative material 80 can also be mixed with ice if available and desired in order to produce an even greater cooling effect.

In other embodiments, the thermal material 26 could be any suitable thermal material, such as ice, an ice and water mixture, cold water, frozen Thermal Gel Bead packs or a cold pack, such as the Dynarex Instant Cold Pack. In further embodiments, the thermal material 26 located inside the interior 44 of the container 22, with the addition of a thermal material applied to the outside of the container, such as a cold pack wrapped around the outside of the container 22 for greater cooling effect. In other embodiments, the container 22 is configured to include a thermal material as an integrated part of the sidewall 40, bottom 42, or both in the form of an insulated container 22.

Figure 18:
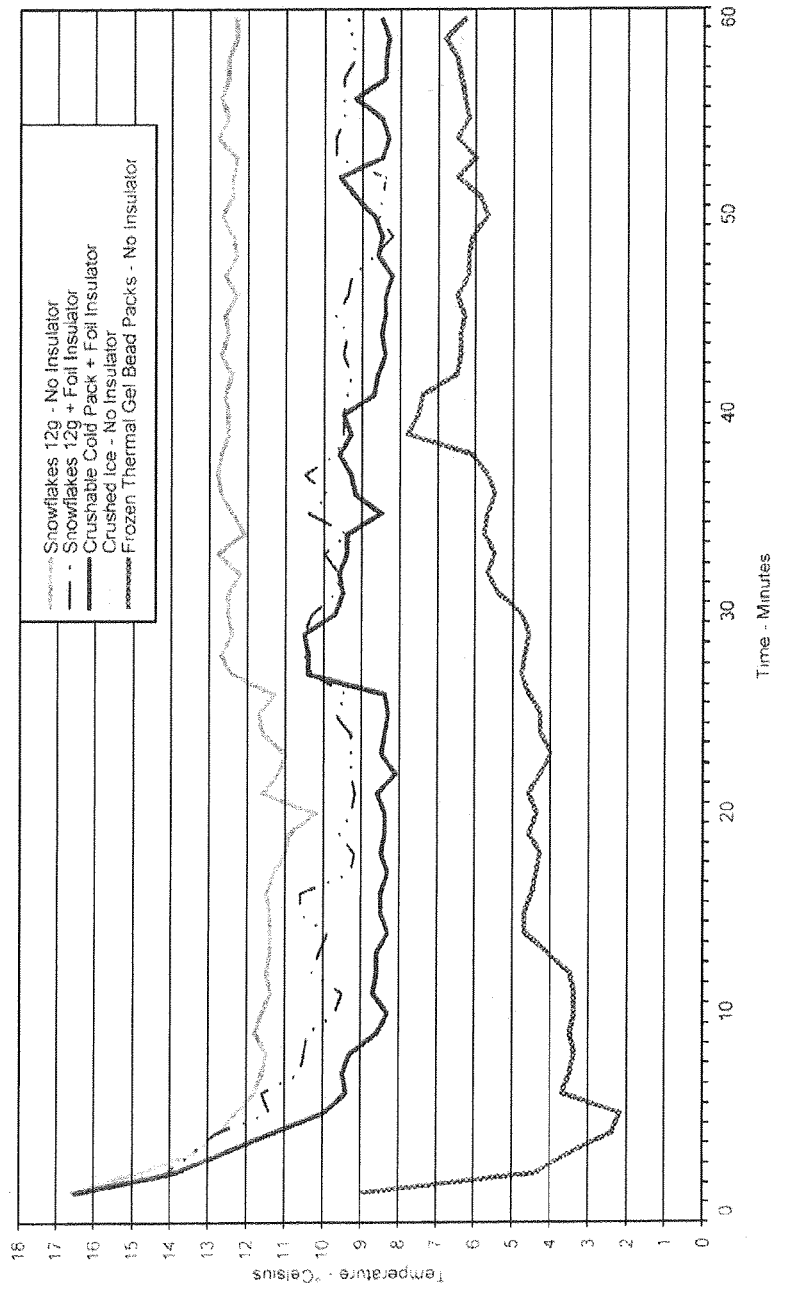
FIG. 18 is a chart illustrating five mist cooling configurations for the Thermal Nebulizing System.

The cooling temperatures of various types of thermal materials 26 used in conjunction with various delivery mechanisms 30 can be seen in the graph of FIG. 18. In a controlled environment this device predictably chilled nebulized mist to a Celsius temperature significantly less than ambient temperature for one hour. FIG. 18 compares four types of Thermal medium for cooling liquid that is nebulized to a chilled mist. Four of the five configurations tested remained consistently under 10 degrees Celsius at the eight minute mark until termination of testing. The fifth configuration remained under 13 degrees Celsius from the five minute mark until termination of testing. All configurations indicate a slight increase in temperature when additional fluid was added to continue adequate mist production. The optional disposable insulator is a foil backed bubble wrap chosen for its lightweight yet effective insulating properties. Testing was terminated at one hour as this best reflects the longest expected transport time for the patient to a hospital or Medical Center.

Returning to FIG. 7, the tubing 82 is configured to be connected to the connector nipple 48 to deliver a gas to the nebulizer 28. The tubing 82 connects to the connector nipple 48 in any suitable way, such as snuggly fitting the tubing 82 over the connector nipple 48, snuggly fitting the connector nipple 48 over the tubing 82, or screwing the tubing 82 and connector nipple 48 together with a threading system.

As shown in the figures, the container bottom 42 is concave and has a plurality of radially oriented ridges 45. However, the bottom 42 can be formed without the ridges 45 and, in some configurations can be flat.

The tubing can be any size sufficient to deliver the required amount of gas to the nebulizer 28, but is preferably between ¼ inch and ¾ inch. The tubing 82 is connected to a gas source (not shown) on the opposite end from the connector nipple 48. The gas source can supply natural air, oxygen, or other suitable compressed gas source. The gas source is preferably set to deliver gas through the tubing at 8 Liters/minute, but can be set to any desired level. The tubing can be any length suitable to connect the thermal nebulizing system 20 to the gas source, but is preferably between 3 feet and 10 feet long.

FIGS. 8-11 show the thermal nebulizing system 20 with an animal mask 90 as the delivery mechanism. The animal mask 90 can be used to deliver therapeutic nebulizing techniques to animals 103. The animal mask 90 is configured to be placed over the mouth, snout, beak or trunk of an animal without harming the animal, in order to deliver nebulized mist to the animal's air passages. The animal mask 90 can be connected directly to the connector 32, the access tube 52, or it can be connected to the connector 32 via the flexible tube 34 in order to give greater reach to the mask 90.

Figure 8:
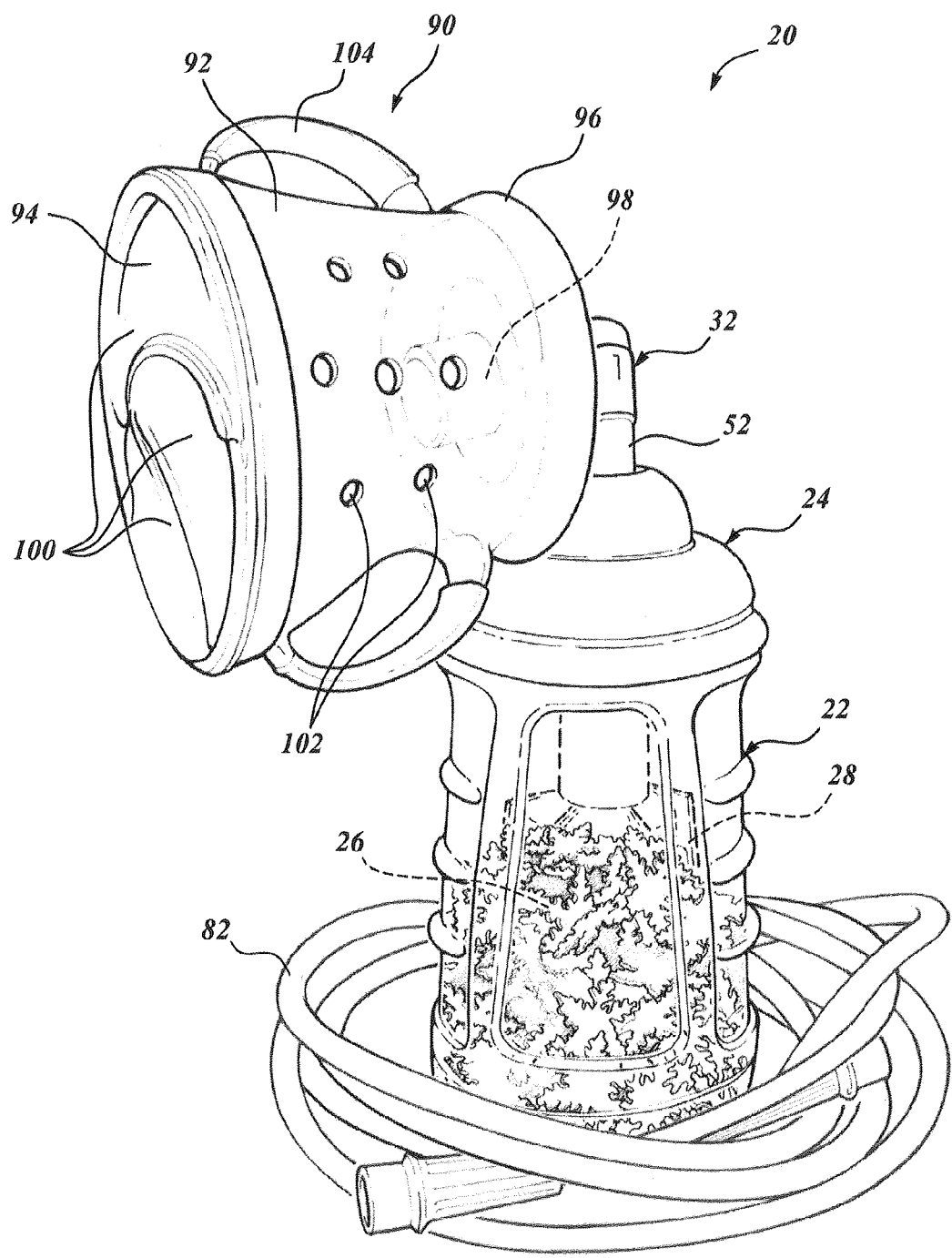
FIG. 8 is an isometric view of a thermal nebulizing device that includes a mask configured to be used with animals or birds according to one embodiment of the present disclosure.
Figure 9:
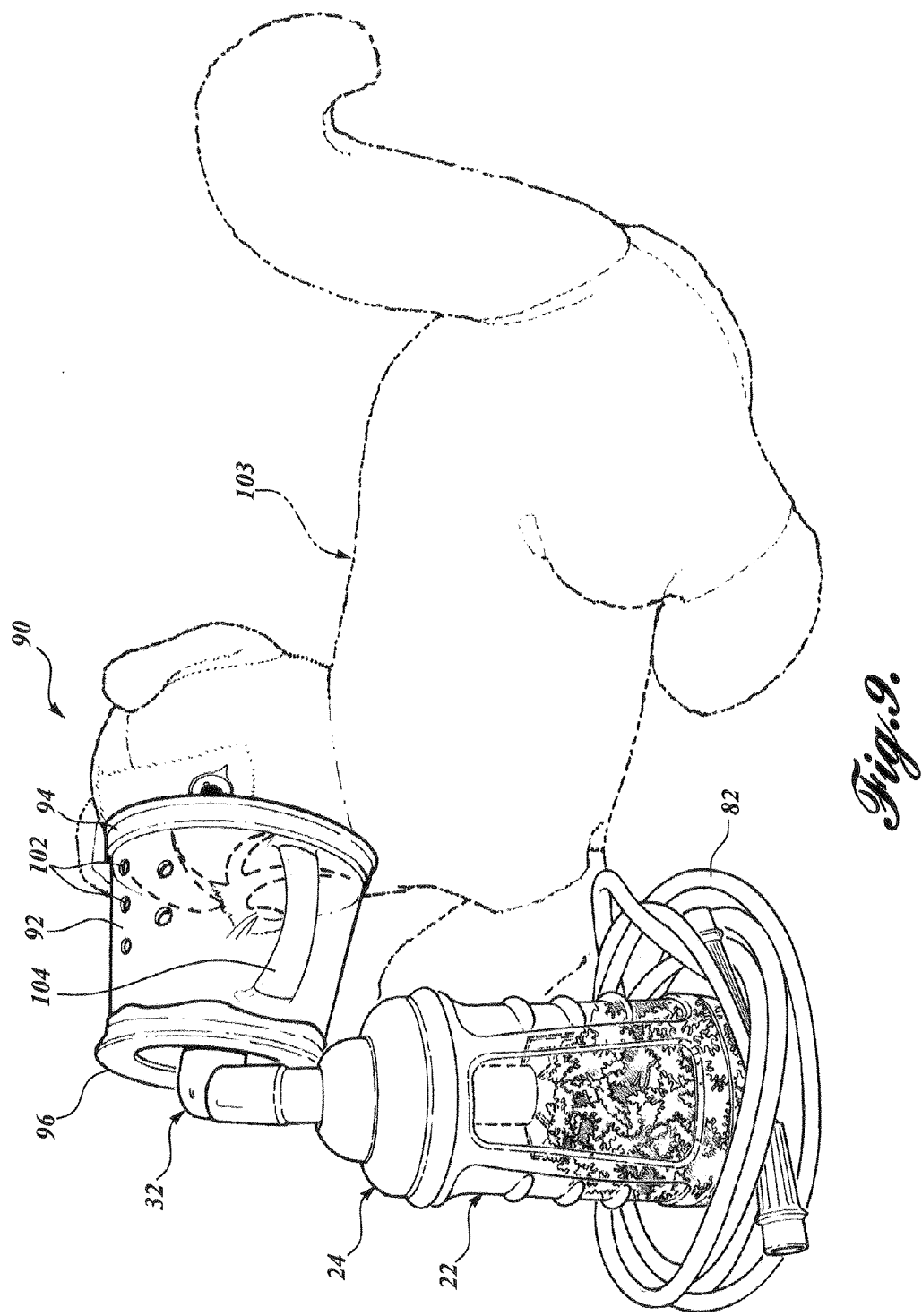
FIG. 9 is an isometric view of the nebulizing device of FIG. 8 illustrating an animal using the nebulizing device.

In the illustrated version of FIGS. 8 and 9, the mask 90 has a circular sidewall 92, a removable petal cap 94, and a bottom wall 96 that together define an interior chamber 93. The mask 90 also includes an access point 98 that is structured as an input port for fluid communication with the interior chamber 93. The sidewall 92 can be either substantially straight, perpendicular to the bottom wall 96 and removable petal cap 94 or angled with respect to the bottom wall 96 and removable petal cap 94 to create a tapered sidewall 92. The sidewall 92 and bottom wall 96 are preferably made of light weight, rigid material such as plastic, but can also be made of a flexible material in order to facilitate easier storage and portability. The access point 98 is preferably located in the bottom wall 96, and is generally a hole in the bottom wall, or a hollow cylinder in the bottom wall 96 through which the animal mask 90 is connected to either the connector 32 or the tube 34. The access point 98 is of sufficient size to connect to the connector 32 or the flexible tube 34, either through snug fitting, a threaded screw type connection, or other suitable semi-air tight connections. Other embodiments of the access point 98 may include an L-shaped cylindrical port for direct connection to the access tube 52 or for connection to the connector 32 or tube 34.

The removable petal cap 94 attaches to the sidewall 92 of the animal mask 90. The petal cap 94 can be attached through any means, including, without limitation, a slip on fitting, a rib-to-rib snap fitting, rib-to-depression snap fitting, and a screw type fitting. In embodiments where the sidewall 92 is made of a flexible material, a rigid connective part may be located on the edge of the sidewall 92 in order to facilitate easier connection between the petal cap 94 and the sidewall 92.

Figure 11:
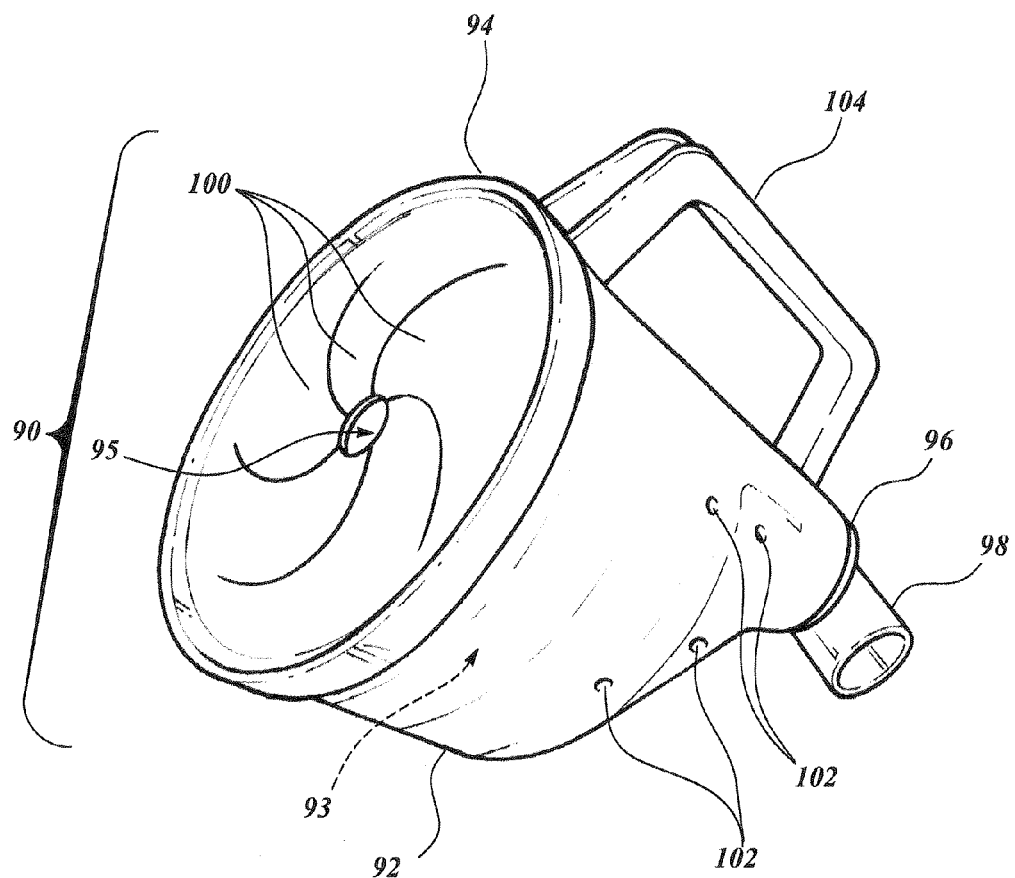
FIG. 11 is an enlarged isometric view of the mask of FIG. 10.

The petal cap is made of several flexible flaps that are arcuate-shaped petals 100, which are connected around the outer edge of the petal cap 94 and come together near the center of the petal cap. As shown in FIG. 11, the petals 100 are sized and shaped to leave a circular opening 95 at the center of the cap 94 that is in fluid communication with the interior chamber 93.

The petals 100 are radially oriented and designed to bend or flex centrally inward, flexing along the connected edge, and provide a sealable opening about an animal's muzzle, beak or trunk when inserted into the animal mask 90. When no animal is utilizing the mask 90, the petals 100 return to a natural state, in which they are positioned roughly perpendicular to the sidewall 92, and abut each other to substantially close off the interior of the mask 90. The petals 100 allow for a safe, snug fit between the animal mask 90 and an animal, while keeping dust and other contaminants out of the mask 90 while not in use. The sidewall 92 or bottom wall 96, or both, may also contain a series of holes 102, which are configured to enable ambient air to mix with the nebulized mist when the animal 103 is using the nebulizing system 20 and provide easy exhalation.

The animal mask 90 may also optionally contain handles 104. The handles 104 can be either permanently fixed to the mask 90 or removably attachable to the sidewall 92 through any suitable means, such as a slot/insert mechanism or a hook and look mechanism, such as Velcro. Preferably, the handles are located on the sidewall 92; however, they may also be located on the bottom wall 96 or petal cap 94. The handles allow for a user to hold the animal mask 90 more comfortably, steadily and without obstructing the holes 102.

Figure 10:
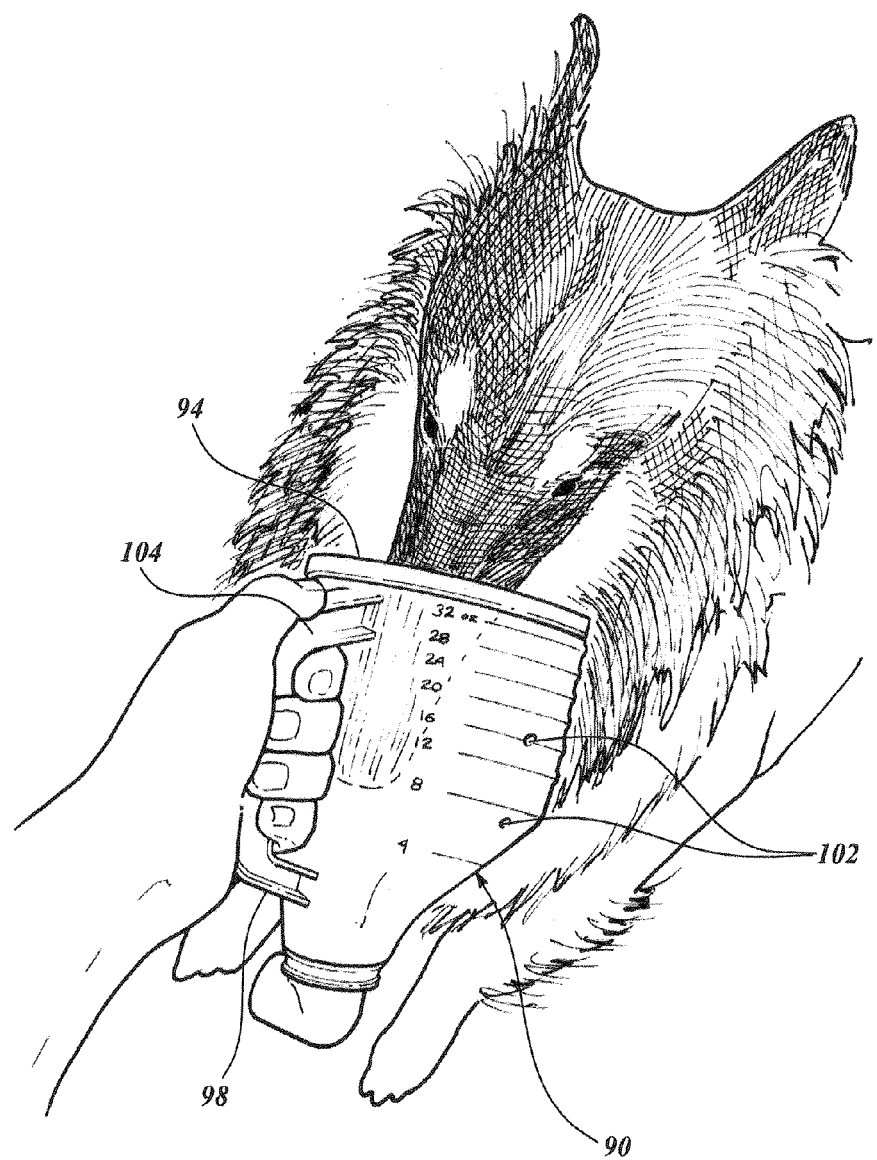
FIG. 10 is an isometric view of a mask being used with an animal according to one embodiment of the present disclosure.

The animal mask 90 can be made in a variety of sizes and shapes in order to be used with a variety of animals, as shown in FIG. 10. Animal masks 90 that are of similar shape, but different size could be nested together, with smaller masks 90 inside larger masks 90, in order to reduce the storage space necessary and increase portability and mobility of the masks 90. The mask 90 may also include a strap or resilient filament connected to the sidewall 92 or elsewhere to aid in holding the mask 90 to the animal's head.

Figure 12:
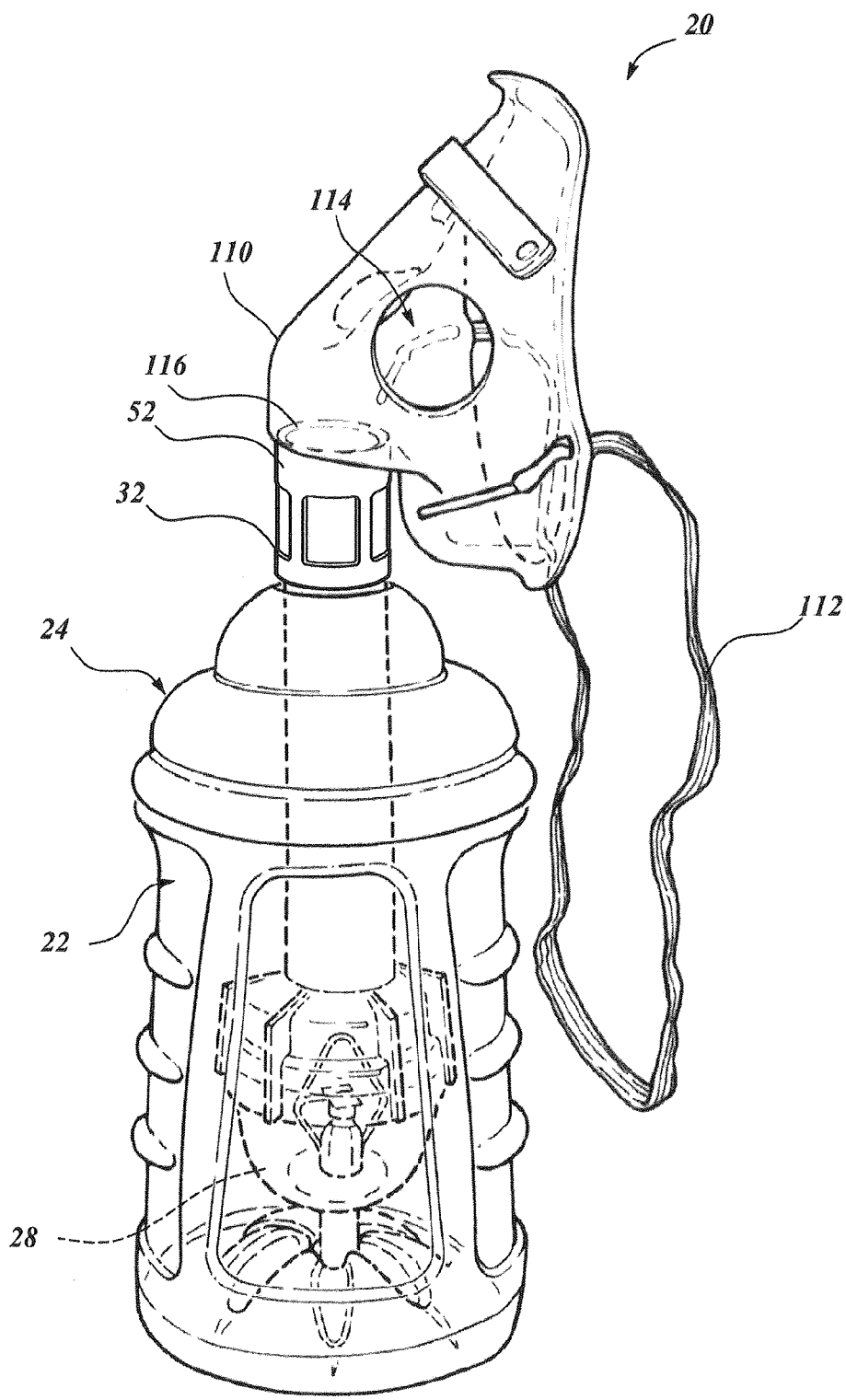
FIG. 12 is an isometric view of a thermal nebulizing device that includes a mask to attach to a recipient's face according to one embodiment of the present disclosure.
Figure 13:
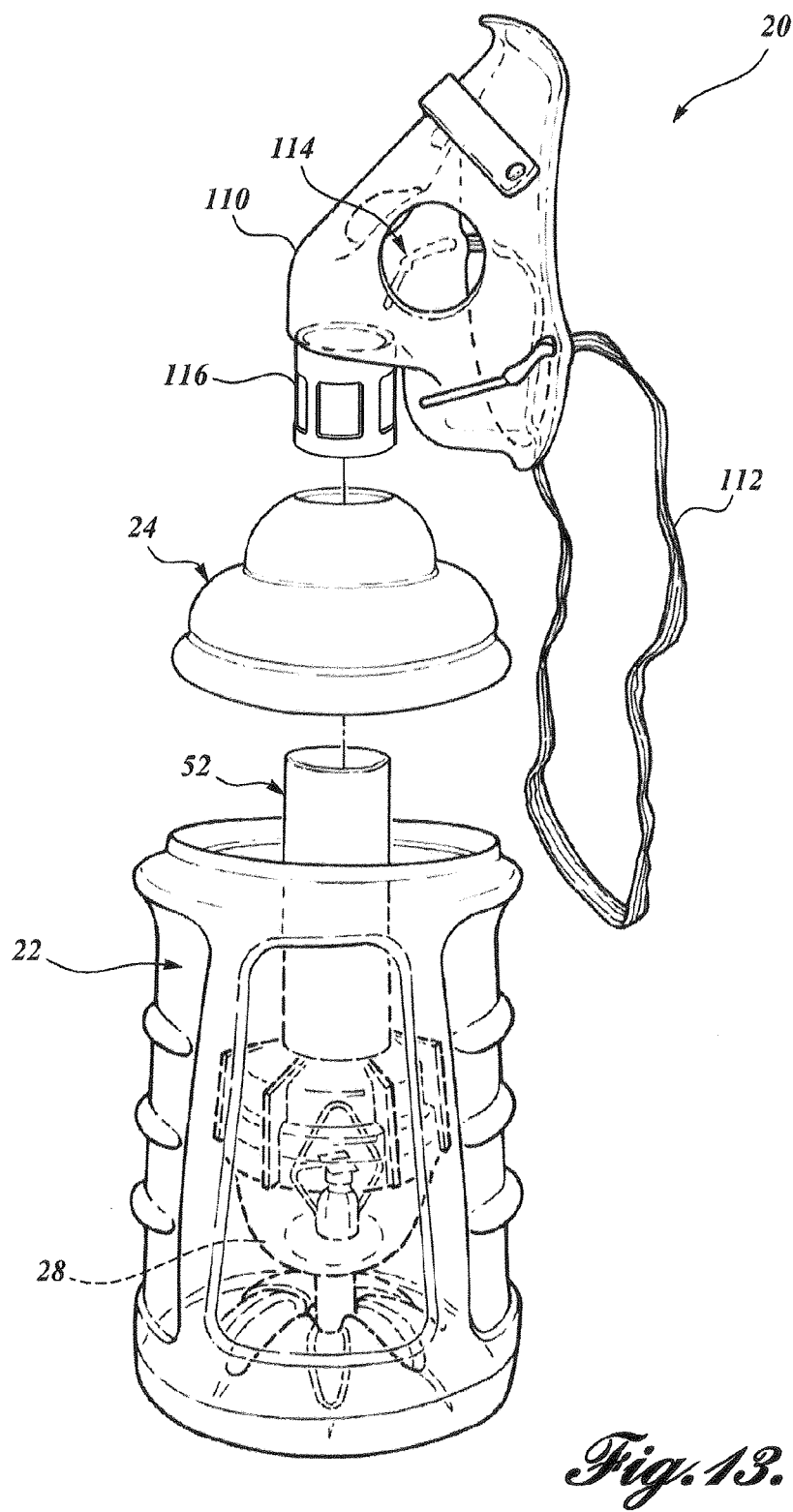
FIG. 13 is a partially exploded view of the nebulizing device of FIG. 12.

FIGS. 12 and 13 show the thermal nebulizing system 20 with an attached face mask 110 as the delivery mechanism 30. The face mask 110 attaches to the thermal nebulizing system 20 through the connector 32 or may connect directly to the access tube 52. The face mask 110 may also connect to either the access tube 52 or connector 32 through the tube 34 in order to allow for greater mobility. The face mask 110 is generally shaped to fit around the mouth and lower face of a patient, and can be held in place by a flexible, reliant one-piece strap 112. The strap 112 connects to the face mask through any suitable means, such as using an adhesive or tying the strap on, and is used to hold the face mask 110 to the patients face without the need for the patient to perform any task in order to keep the face mask 110 on the lower face. The mask 110 also contains an access or attachment point 116, in order to allow for connection with the nebulizer 28. The access point 116 may be a generally circular opening in the face mask, or it can be a straight or bent hollow cylindrical tube located in the mask. The access point 116 connects to the nebulizer 28 through the access tube 52, connector 32 or tube 34. The face mask 110 also may contain one or more relief holes 114 that allow a patient to exhale normally and ambient air to mix with the nebulized mist. The face mask 110 can be made in a variety of sizes in order to fit a variety of patients who may require the use of the mask due to limited ability to use one of the alternate delivery mechanisms 30.

Figure 14:
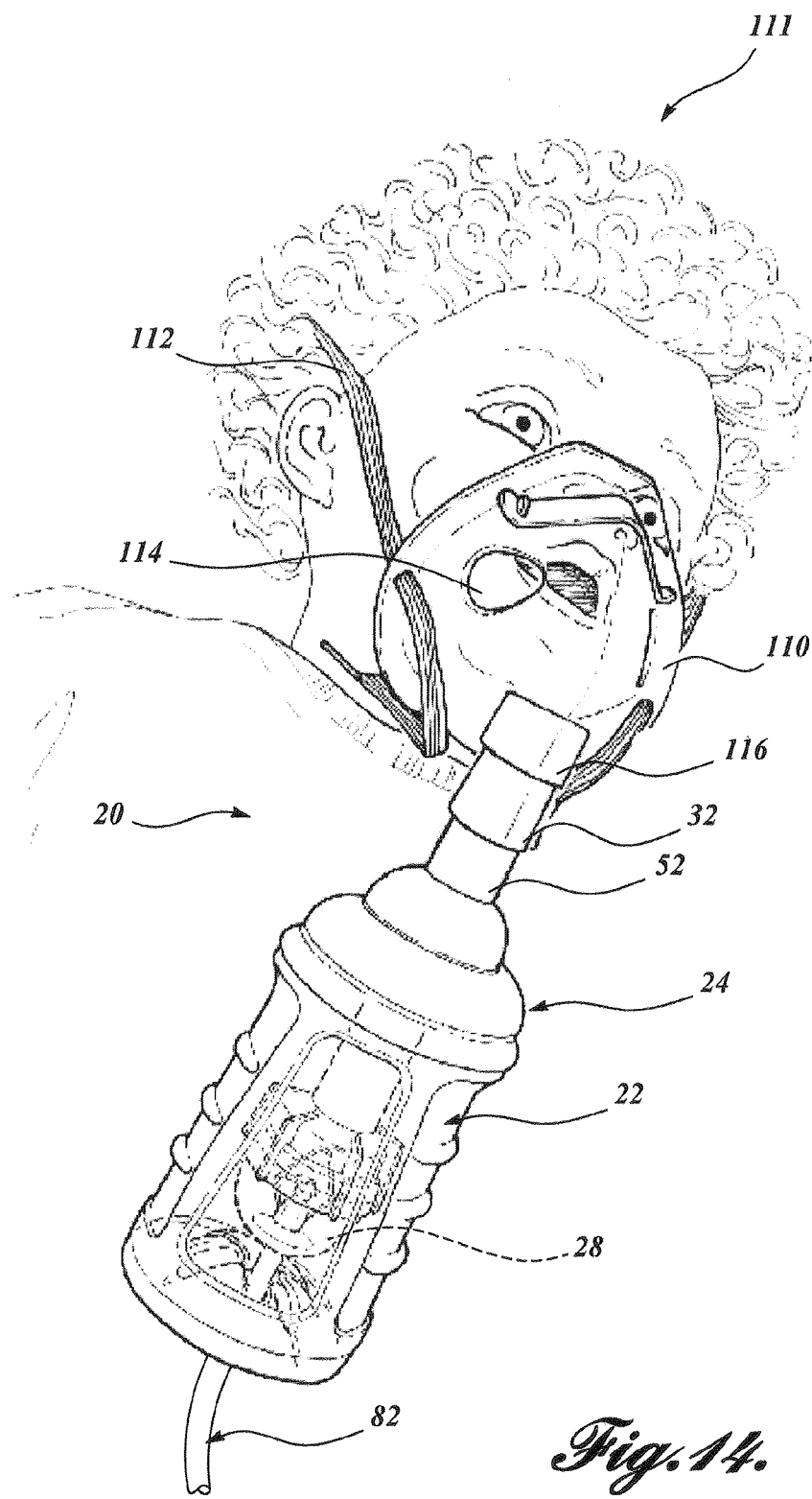
FIG. 14 is an isometric view of the nebulizing device of FIG. 12 shown being used by a child.

FIG. 14 illustrates the thermal nebulizing apparatus 20 of FIG. 12 being used on a pediatric patient 111. Pediatric patients are often unable to effectively use many of the alternate delivery mechanisms and, therefore, must utilize the face mask 110 in order to use the thermal nebulizing system 20 for a beneficial amount of time. The patient places the face mask 110 on their face and then places the strap 112 behind their head in order to hold it in place then breathes normally. Alternately, a caretaker may place the face mask 110 and strap 112 on the patient if they are unable to do so.

Figure 15:
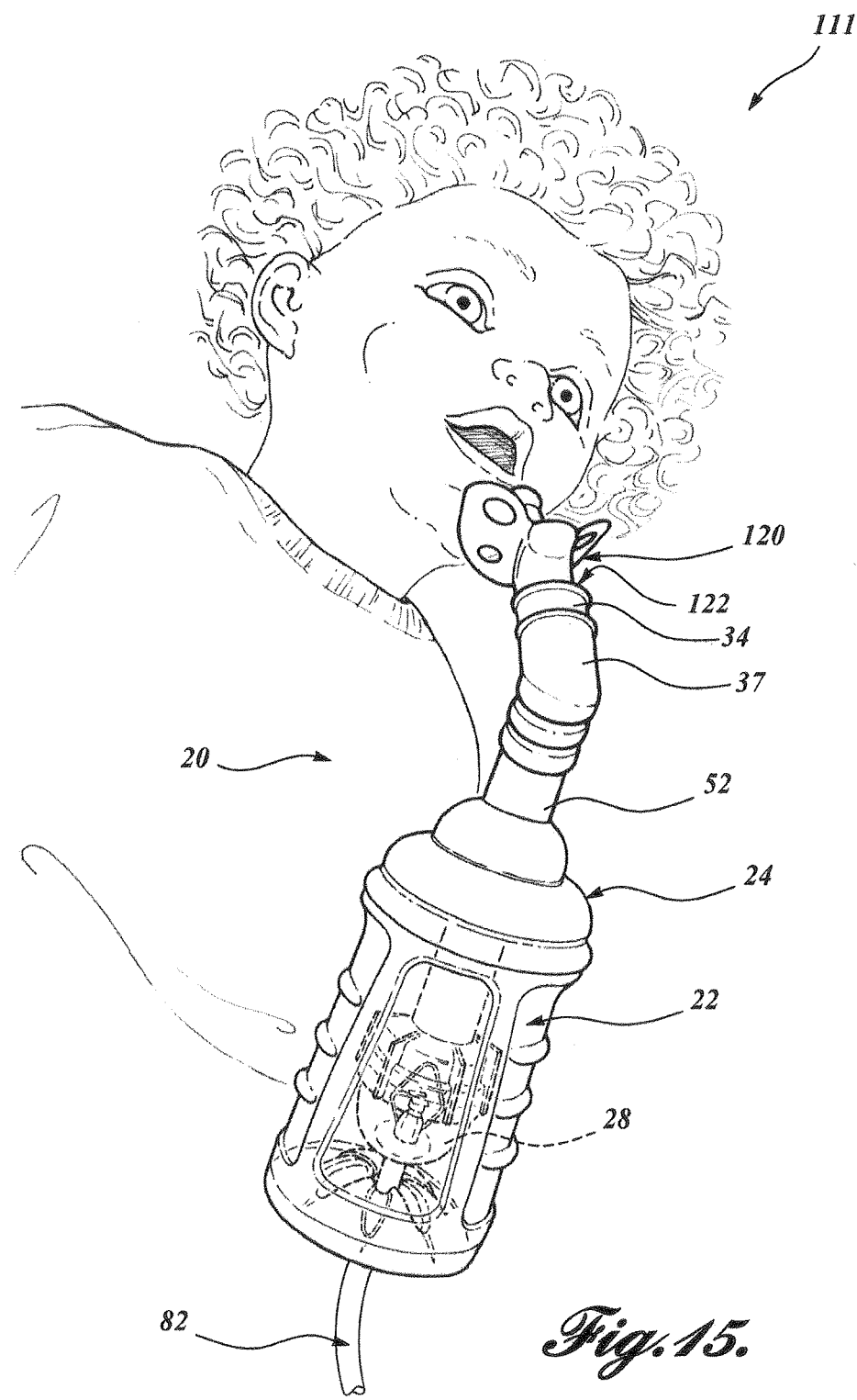
FIG. 15 is an isometric view of a thermal nebulizing device with a pacifier mist delivery device according to one embodiment of the present disclosure.

FIG. 15 shows the thermal nebulizing system 20 with an attached pacifier mist delivery device 120. The pacifier mist delivery device 120 is intended for use with pediatric patients 111 in order to ease the transition into breathing in nebulized mist by using a device familiar to most pediatric patients. The pacifier mist delivery device is generally in the shape of a standard pacifier and contains an air channel that goes the length of the pacifier to allow nebulized mist to be breathed into through the nostrils of an infant 111 while using the pacifier mist delivery device 120. The channel connects to an access point 122, which is connected to the thermal nebulizing system 20 through a tube 34, the connector 37 or directly to the access tube 52.

Figure 16:
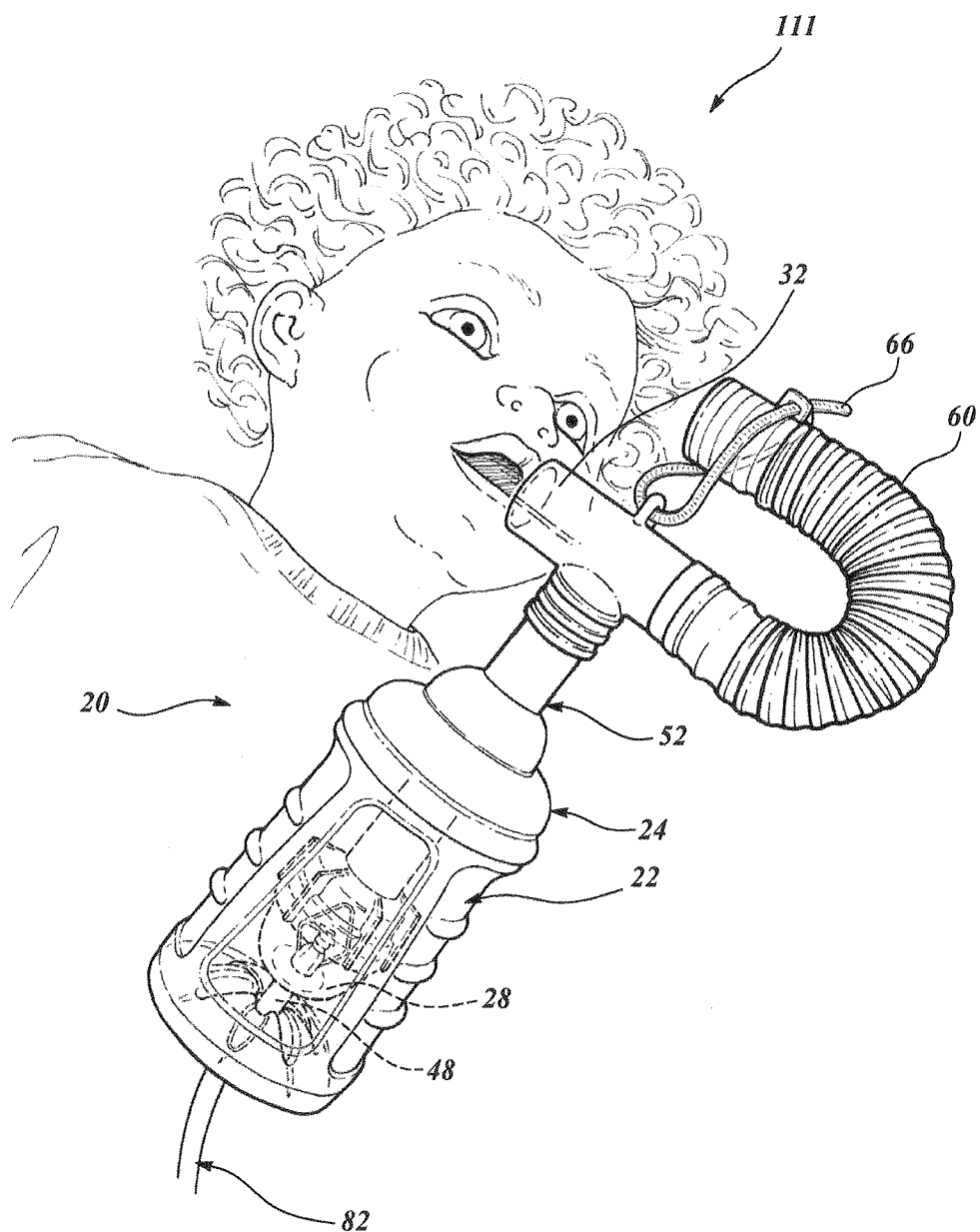
FIG. 16 is an isometric view of a thermal nebulizing device having a dual port T-connector and supply tubing according to one embodiment of the present disclosure.

FIG. 16 shows the thermal nebulizing system 20 with an attached corrugated tube 60 being used on a patient. The corrugated tube 60 is preferable attached to a T or Y shaped connector 32, opposite the end where a patient 111 interfaces with the thermal nebulizing system 20. The corrugated tube acts as a reservoir to collect various droplets contained in the mist, as well as an exhalation point and a point for air to mix with the nebulized mist for inhalation. The corrugated tube may be bent and attached to the connector 32 in order to allow for more effective catching of debris and mist droplets. When bent, the corrugated tube 60 may bend to about 180 degrees, though other bends may be desirable. When bent, the corrugated tube 60 is generally attached to the connector 32 at the attachment point 64 through any suitable attachment mechanism 66, such a twist tie or cable tie.

Figure 17:
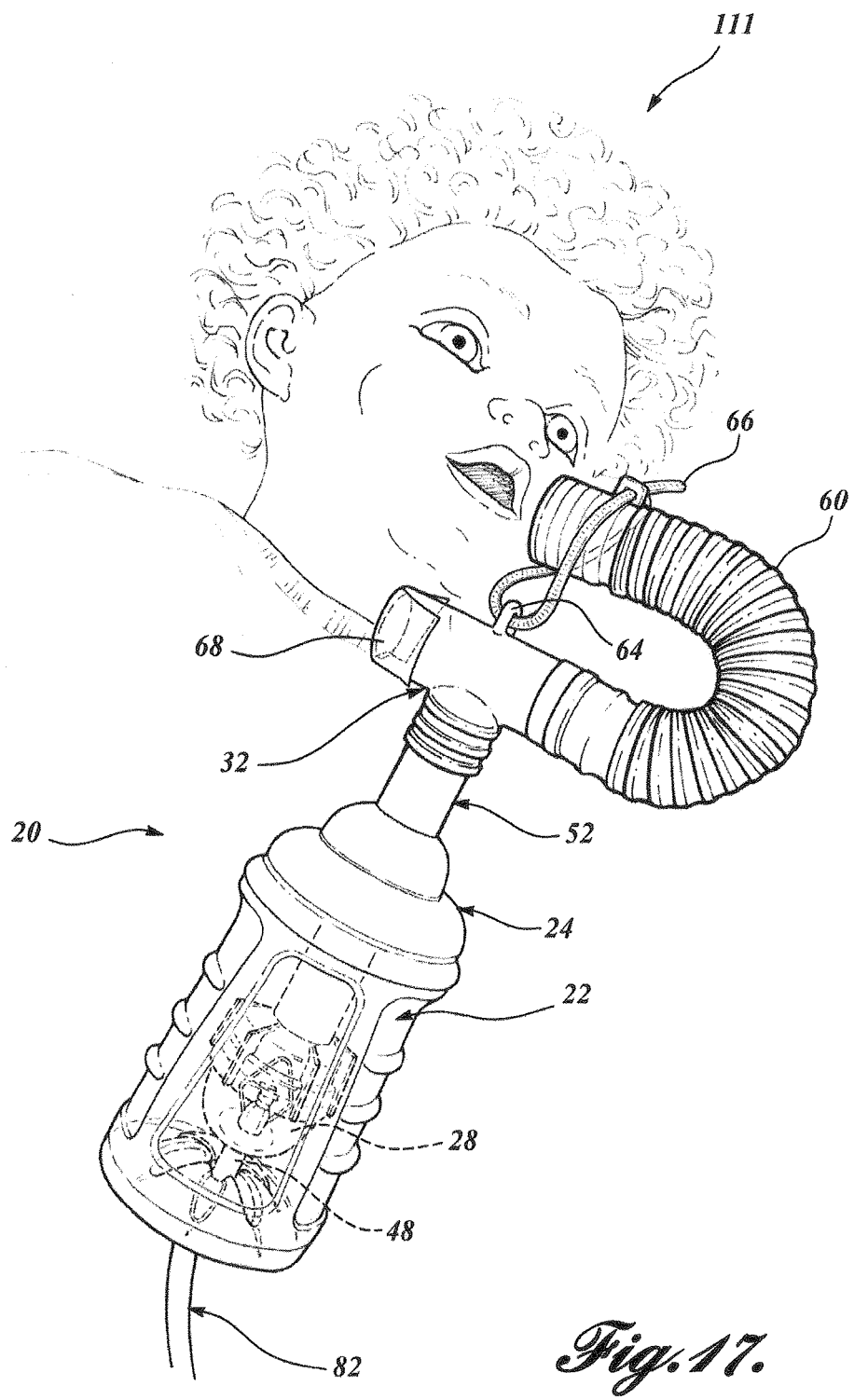
FIG. 17 is an isometric view of the nebulizing device of FIG. 16 illustrating a dual-port embodiment in which one end of the T-connector is blocked off according to one embodiment of the present disclosure.

FIG. 17 shows the thermal nebulizing system 20 of FIG. 16, in which a patient interfaces with the corrugate tube 60 to obtain the nebulized mist. The port on the opposite end of the connector 32 may optionally be plugged or covered by any suitable covering mechanism 68, such as with tape, a patient's hand or finger, or the cover 36 (see FIG. 1) may be used. Alternatively, the port on the opposite side of connector 32 may be left open. The corrugated tube 60 serves as a collection device, retaining any large droplets in the nebulized mist to prevent the patient from inhaling these droplets. The corrugated tube 60 can also be used to direct the flow of the mist.

The chilled mist has a number of therapeutic properties, including fast acting therapy to initiate Therapeutic Hypothermia, treatment of multiple respiratory illnesses such as croup, laryngobronchitis, and others, and can produce a more comfortable nebulized mist for patients who regularly use a nebulizer. The thermal nebulizing system 20 is particularly beneficial to emergency medical professionals: allowing earlier initiation of Therapeutic Hypothermia with the potential to drastically improve patient outcomes in cases of cardiac arrest, anoxic encephalopathy and others.

Traditionally, a number of techniques may be used to induce hypothermia, such as cooling pads, intravenous devices and intranasal wands, however, these devices are generally not used until the patient is already at a hospital or other medical facility. The thermal nebulizing system 20, on the other hand, is capable of initiating Therapeutic Hypothermia in a mobile setting, allowing first responders to use the system 20 in order to begin life saving techniques much earlier. The thermal nebulizing system 20 also is simple enough for home use or use by medical professionals without costly and time consuming training. Furthermore, the simple design of the system allows for low costs, and thereby allows the system to be treated as a one-time use system if desired in order to improve health and safety of the system.

As will be readily appreciated from the foregoing, the device and system of the present disclosure provides a rapid, simple method to deliver chilled oxygen, mist or medication to treat, improve or reverse symptoms related to the respiratory system, heat related illness, and initiation of Therapeutic Hypothermia to alleviate illness and suffering.

It is widely accepted medical practice that the application of ice to injured tissue reduces swelling, inflammation and pain. There have been many attempts in the past to apply this practice to the respiratory system. The disclosed thermal material nebulizing system is portable and requires no electrical connection to initiate cooling once a thermal medium is chosen for the application. This thermal material nebulizing system does not require effort from the patient to initiate the mist as it is a continuous flow until the airflow is disconnected.

The historical development of Therapeutic Hypothermia (TH) dates back millennia, and has been actively used by "modern" clinical medicine for the last two hundred years. Routine use of TH has been employed in the Operating Room for the past fifty years. Numerous clinical trials have used TH to reduce the core body temperature to 32-34 degrees C. Early recognition of the need for TH and the rapid initiation of TH have improved both chances of survival and neurological outcome. Current TH treatment involves various methods to cool a patient's core temperature of 32-34 degrees C. within four hours of insult to reduce the risk of tissue damage following a period of insufficient blood flow either within the brain or the myocardium (heart attack), or throughout the body as a result of cardiac arrest. Multiple invasive methods are currently in use to maintain the core temperature within the designated range for approximately twenty-four hours.

The American Heart Association has released guidelines indicating Therapeutic Hypothermia as a Class 1 evidence for surviving STEMI (heart attack), plus cardiac arrest. Targeted Temperature Management is now recognized as a valid treatment for other Hyperthermia related illness like Malignant Hyperthermia, Heatstroke and Febrile Sepsis.

The missing link in the chain of survival for patients needing rapid cooling has been the lack of a noninvasive portable inexpensive device that can deliver cooling to the core circulation via the respiratory system. The disclosed noninvasive thermal material nebulizing system is for single patient use. The ergonomic, light weight easy use design can be used to deliver chilled mist to adults, children, infants, newborns and animals with beaks, trunks, or snouts for cooling via mask, mouth piece, pacifier mist delivery device (for infants), Aerosol Delivery Hood/Tent, Endotracheal tube, Blow-by and Bipap (noninvasive ventilation).

Various types of insulators have been tested including but not limited to Neoprene, Foil backed bubble wrap, plastic bubble wrap, Thermal evaporative material, foam.

Venues of Application and Use

Chilled mist via the disclosed thermal material nebulizing system can be used:

In any venue with a supply of compressed oxygen, air or accessible portable nebulizer compressor to treat Epiglottis, Croup, RSV, Bronchospasm, Fever, Allergic Reaction, Smoke Inhalation, Blast Injury, Asthma, Bronchitis, Pneumonia, Laryngitis, Sepsis, COPD, ventilated patients, and pre and post ENT surgery.

In any venue with a supply of compressed oxygen, air or accessible portable nebulizer compressor.

To initiate core cooling during CPR.

To initiate Therapeutic Hypothermia in any venue.

As an adjunct during Targeted Temperature Management.

By Paramedics/Flight Nurses/Military medics to initiate Therapeutic Hypothermia post Cardiac Arrest.

In Emergency Departments, Intensive Care Units, Coronary Care Units, Critical Care Units and Operating Rooms to initiate or continue Therapeutic Hypothermia post Cardiac Arrest.

By Paramedics, Military and Emergency Department medical personnel immediately upon recognition of myocardial infarction to initiate Therapeutic Hypothermia prior to re-vascularization in the Cardiac Catheterization Lab.

By Pre-Hospital, EMS Paramedic/Firefighters/Flight Nurses/Military Medic, emergently treating Croup, RSV, Epiglottitis, Allergic Reactions, Bronchospasm, Laryngitis, Pneumonia, Asthma, COPD, Bronchitis, Heat Stroke and other heat related illness, heat/blast/smoke/exposure injury/inhalation, Sepsis and other airway compromising conditions.

By Emergency Department Personnel emergently treating Croup, RSV, Epiglottitis, Allergic Reactions, Bronchospasm, Laryngitis, Pneumonia, Asthma, COPD, Bronchitis, Heat Stroke, heat/blast inhalation/exposure/injury, other heat related illnesses (chemically induced hyperthermia), Sepsis and other airway compromising conditions.

In the Neurological ICU to initiate Therapeutic Hypothermia post Cerebral Vascular Accident and other Neurologic Hyperthermia related events.

In the ENT postoperative setting to chill the mouth, nasopharynx and upper respiratory tract to decrease bleeding, swelling and to aid in pain control.

To initiate tissue chilling by EMS, Emergency Department, Military medical and Wilderness Medical personnel for facial trauma to reduce nasopharyngeal and oral swelling and to aid in pain control.

By Anesthesiology in the Operating rooms and ICU's to treat Anesthesia induced Hyperthermia by delivering chilled mist/medication/oxygen/air to the patients core via endotracheal tube, tracheotomy tube via Triple port nebulizer T-connector, mask, or mouth piece to initiate Therapeutic Hypothermia.

By the patient at home for the treatment of Croup, Bronchitis, Asthma, COPD and other airway compromising illnesses.

To connect to endotracheal (32) or tracheotomy tubes to initiate Therapeutic Hypothermia by delivering chilled mist/medication/oxygen/air to the patient's core.

On airplanes, trains, and cruise ships.

On space shuttle and space stations.

By Pre-Hospital EMS Paramedics, Firefighters and/or Veterinarians emergently treating Animal airway compromise due to heat/smoke/inhalation/exposure or heat related illness via the Animal Rescue Mask.

By Veterinarians in animal hospitals, clinics, zoos, and outpatient settings in treating asthma, allergic reaction and other airway compromising illnesses via the Animal Rescue mask.

Figure 19:
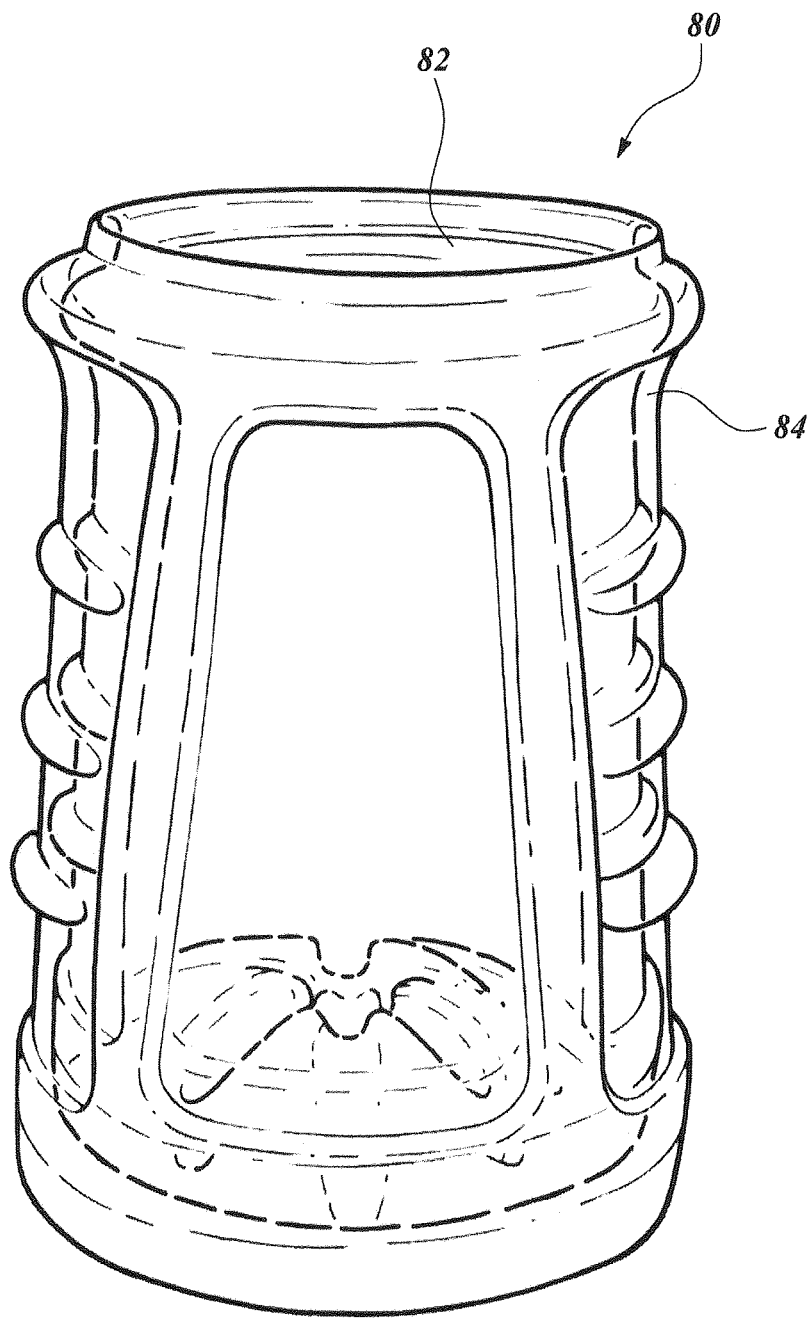
FIG. 19 is an isometric view and FIG. 20 is a partial cut-away isometric view illustrating a doubled wall configuration of the thermal nebulizing container in accordance with another aspect of the present disclosure.
Figure 20:
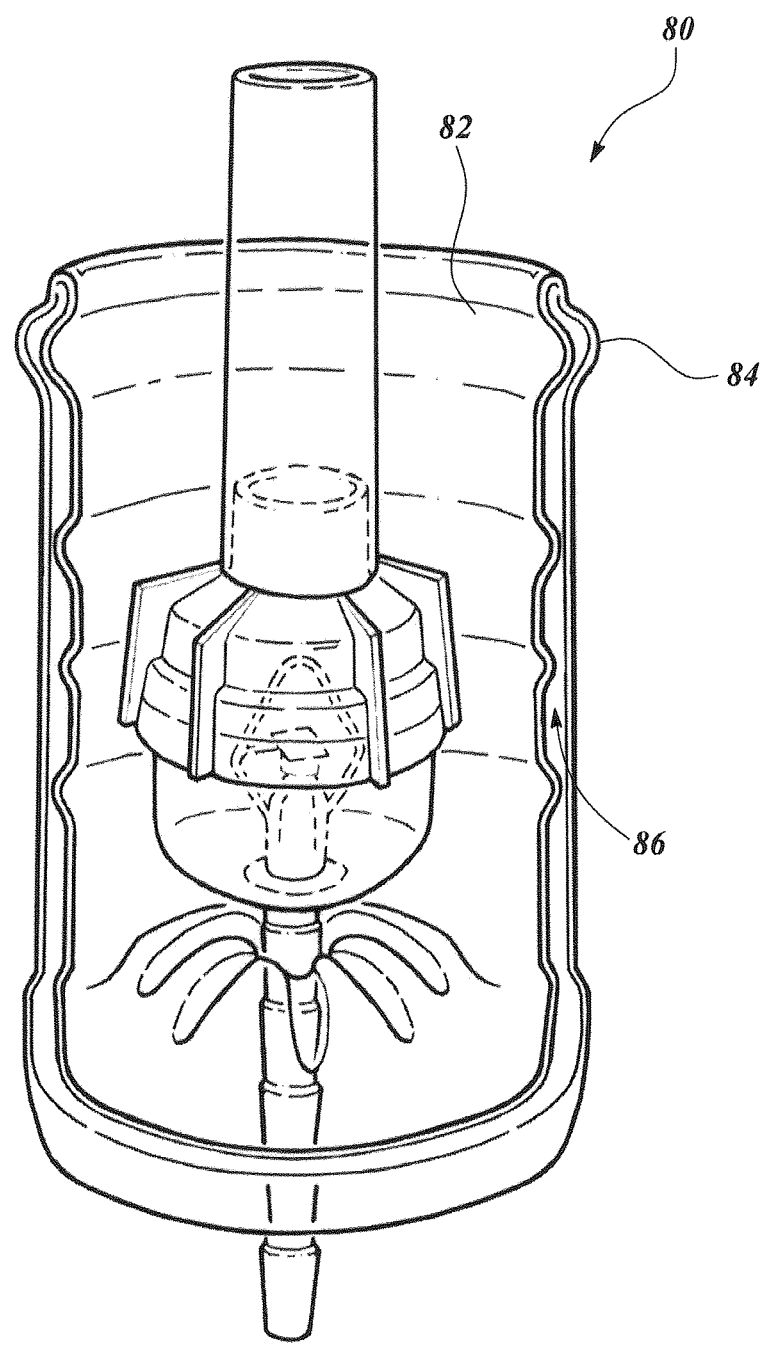

The various embodiments described above can be combined to provide further embodiments. Aspects of the embodiments can be modified, if necessary to employ concepts of the various patents, applications and publications to provide yet further embodiments. For example, FIGS. 19 and 20 illustrate a double-walled configuration of a container 80 in which an inner wall 82 is integrally formed with an out wall 84. This design creates an air space 86 between the two walls 82, 84. In accordance with one aspect of the present disclosure the air space 86 serves to insulate the interior of the container. Not only does this configuration maintain the cool temperature within the container 80, it allows the user to hold the outer wall 84 for a prolonged period of time. Alternatively, the air space can contain the thermal material, either as an integrated part of the container as described above or as a refillable space through an opening in the outer wall 84.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A portable nebulizing device for use with a pressurized gas to generate a chilled mist from a liquid cooled by a thermal cooling material, the portable nebulizing device comprising:

a hand-holdable portable container having a side wall and a bottom wall that together define an interior to hold a fixed amount of the thermal cooling material, and an open top in communication with the interior, and only one input port in the bottom wall;

a small-volume jet nebulizer located in the interior of the container, the nebulizer including a housing having an opening, a removable top to cover the opening, and a bottom that together define an enclosed interior space to hold a fixed amount of the liquid to be nebulized, the bottom having a fluid input in fluid communication with the interior space, and the removable top having a fluid output to be in fluid communication with the interior space when the removable top is covering the opening, and the fluid input coupled to the input port of the portable container that provides fluid communication with the interior space to receive a pressurized gas for input into the interior space of the nebulizer, the nebulizer capable of generating a chilled mist from the fixed amount of liquid in response to introduction of the pressurized gas into the interior space of the nebulizer;

a lid to cover the open top of the container and enclose the nebulizer in the interior of the container and to hold the fixed amount of the thermal cooling material to surround the nebulizer from the bottom to the top thereof within the interior of the container;

a conduit to be coupled to the fluid output of the removable top of the nebulizer and to pass through the lid of the container and further to provide fluid communication from the interior space of the nebulizer through the lid to permit the chilled mist from the nebulizer to pass to an exterior of the container; a nipple coupled to the container input port to provide fluid communication between the input port and the fluid input of the nebulizer, the nipple sized to position the nebulizer above the bottom wall of the container and permit thermal cooling material to surround the nebulizer from the bottom to the top of the nebulizer and cool the liquid in the interior space of the nebulizer.

2. The device of claim 1, wherein the bottom wall of the container is concave and includes a plurality of radially oriented ridges, and the lid has a two-tiered convex dome shape.

3. A portable system for generating a chilled mist from a liquid and delivering the chilled mist to a recipient, comprising:
   a thermal cooling material configured to chill the liquid;
   a small-volume jet nebulizing device that is capable of nebulizing the chilled liquid into the chilled mist, the nebulizing device including a housing having an opening, a removable top to cover the opening, and a bottom that define an interior space to retain only a fixed amount of the liquid, the bottom having a fluid input in fluid communication with the interior space to receive a pressurized gas, and the top having a fluid output in fluid communication with the interior space, the nebulizing device configured to generate the chilled mist only from the fixed amount of the liquid in the interior space in response to receipt of the pressurized gas;
   a hand-holdable portable container having a bottom wall, a side wall, an open top, a removable top securable to the side wall and sized and shaped to cover the open top, and an interior sized and shaped to enclose the nebulizing device, the interior capable of receiving and holding the thermal cooling material around the nebulizing device from the bottom to the top of the nebulizing device and chill the liquid in the interior space of the nebulizing device;
   a source of pressurized gas coupleable to the fluid input of the nebulizing device to deliver the pressurized gas to the fluid input of the nebulizing device;
   a delivery apparatus coupleable to the fluid output of the nebulizing device to deliver the chilled mist from the nebulizing device through the removable top and to the recipient; and
   a conduit extending through the container and into the interior of the container, the conduit coupled to the fluid input of the nebulizing device and sized and shaped to convey the pressurized gas from the source of pressurized gas to the fluid input of the nebulizing device.

4. The system of claim 3 wherein the thermal cooling material is an evaporative material.

5. The system of claim 3, wherein the bottom wall of the container is concave and includes a plurality of radially oriented ridges and the conduit is sized and shaped to hold the nebulizing device above the bottom wall of the container and permit the thermal cooling material to surround the bottom of the nebulizing device, and the lid has a two-tiered convex dome shape.

6. The system of claim 3 wherein the delivery apparatus includes a mask having a body with an interior chamber and a cap with radially oriented flaps that are capable of bending inward into the interior chamber, the interior chamber sized and shaped to accommodate the muzzle, snout or beak of an animal.

7. The system of claim 3 wherein the delivery apparatus comprises:
   a T-shaped connector having an input port and first and second output ports, the input port coupled to the fluid output of the nebulizing device top; and
   a delivery device coupled to the first output port that is capable of delivering chilled mist to the recipient's mouth or nose.

8. A nebulizing and delivery apparatus for use with a pressurized gas to deliver a chilled mist from a liquid cooled by a thermal cooling material, the apparatus comprising:
   a small-volume jet nebulizer that is capable of generating a chilled mist from the liquid, the nebulizer having a housing with a gas input and a fluid output, the housing having an opening, a removable top securable to the housing to cover the opening, and a bottom that define an interior space to hold a fixed amount of the liquid, the bottom having the gas input in fluid communication with the interior space to convey the pressurized gas to the interior space, and the removable top having the fluid output in fluid communication with the interior space to receive the chilled mist;
   a hand-holdable portable container having a bottom wall, a side wall, an interior defined by the bottom wall and the side wall to hold the nebulizer and the thermal cooling material, an input port, and an open top in fluid communication with the interior and the input port, the interior sized and shaped to enclose the nebulizer and the fixed amount of the thermal cooling material so the thermal cooling material can surround the nebulizer from the bottom to the top of the nebulizer and chill the liquid in the nebulizer;
   a removable cover to close the open top of the container and completely enclose the nebulizer inside the container, the removable cover having an opening;
   a first conduit mounted in the opening of the removable cover and coupled to the fluid output of the nebulizer to deliver the chilled mist from the nebulizer to outside the container;
   a delivery apparatus operably coupled to the first conduit to deliver the chilled mist from the nebulizer; and
   a second conduit extending through the input port of the container and into the interior of the container, the second conduit coupled to the gas input of the nebulizer to provide the pressurized gas to the gas input of the nebulizer and sized to hold the nebulizer above the bottom wall of the container and enable the thermal cooling material to be located between the nebulizer and the bottom wall of the container and to cover the nebulizer from the bottom to the top of the nebulizer.

9. The apparatus of claim 8, wherein the bottom wall of the container is concave and includes a plurality of radially oriented ridges, and the lid has a two-tiered convex dome shape.

10. The apparatus of claim 8, wherein the delivery apparatus includes a mask having a body with an interior chamber and a cap with radially oriented flaps that are capable of bending inward into the interior chamber, the interior chamber sized and shaped to accommodate a muzzle, snout or beak of an animal and to deliver the chilled mist from the nebulizer to the muzzle, snout or beak of the animal.

11. The device of claim 8, wherein the delivery apparatus includes:
   a T-shaped connector having an input port coupled to the first conduit and further including at least one output port; and
   a delivery device coupled to the at least one output port that is capable of delivering chilled mist to the recipient's mouth or nose.

12. The apparatus of claim 8 wherein the thermal cooling material comprises a wet or dry thermal evaporative material.

13. The apparatus of claim 8 wherein the thermal cooling material is one from among ice, an ice and water mixture, cold water, cold pack, or frozen thermal gel bead packs.

14. The apparatus of claim 8 wherein the container includes a double-walled portion having an interior space to hold the thermal cooling material.

\* \* \* \* \*